(12) United States Patent
Felix et al.

(10) Patent No.: US 10,368,756 B2
(45) Date of Patent: Aug. 6, 2019

(54) SENSING CIRCUIT WITH CASCADED REFERENCE

(71) Applicant: BioPause LLC, Mukilteo, WA (US)

(72) Inventors: Jason Felix, Vashon Island, WA (US); Leslie Ann Chertok, Vashon, WA (US); Laureli Shimayo, Everett, WA (US); Vandana Verma, Mountain View, CA (US)

(73) Assignee: BioPause LLC, Vashon, WA (US)

( * ) Notice: Subject to any disclaimer, the term of this patent is extended or adjusted under 35 U.S.C. 154(b) by 160 days.

(21) Appl. No.: 15/396,113

(22) Filed: Dec. 30, 2016

(65) Prior Publication Data

US 2017/0215745 A1 Aug. 3, 2017

Related U.S. Application Data

(60) Provisional application No. 62/274,119, filed on Dec. 31, 2015, provisional application No. 62/292,486, filed on Feb. 8, 2016.

(51) Int. Cl.

| A61B 5/00 | (2006.01) |
|---|---|
| A61B 5/04 | (2006.01) |
| A61B 5/024 | (2006.01) |
| A61B 5/0245 | (2006.01) |
| A61B 5/0255 | (2006.01) |
| A61B 5/0428 | (2006.01) |

(52) U.S. Cl.
CPC .......... *A61B 5/0245* (2013.01); *A61B 5/0255* (2013.01); *A61B 5/04004* (2013.01); *A61B 5/0428* (2013.01); *A61B 5/486* (2013.01); *A61B 5/681* (2013.01); *A61B 5/725* (2013.01); *A61B 5/7214* (2013.01); *A61B 5/7225* (2013.01); *A61B 5/7275* (2013.01); *A61B 5/7282* (2013.01); *A61B 5/743* (2013.01); *A61B 5/7465* (2013.01); *A61B 5/02438* (2013.01)

(58) Field of Classification Search
CPC .......................... A61B 5/7203; A61B 5/7228
See application file for complete search history.

(56) References Cited

U.S. PATENT DOCUMENTS

| 6,190,314 | B1 | 2/2001 | Ark |
| 8,617,067 | B2 | 12/2013 | Jain et al. |
| 8,666,672 | B2 | 5/2014 | Winarski |

(Continued)

*Primary Examiner* — Gary Jackson
*Assistant Examiner* — Jonathan Kuo

(57) ABSTRACT

This disclosure provides cascaded reference circuits and low amplitude signal sensing circuits that are useful in wearable devices. Circuits for measuring electrovesselgram (EVG) and subdermal spectrogram (SSG) are provided, as well as methods for using these circuits to determine quantities and qualities of a person's moods, such as how much and what kinds of stress they experience. The provided devices are useful on limbs and appendages, such as in a smart watch that is worn on the wrist. Methods are provided for using the devices of this disclosure to privately alert wearers to an increase in bad stress in the moment when they can take actions to reduce their stress and physiological stress responses. These devices are useful for measuring and increasing the effectiveness of relaxation techniques. As a result of using methods and devices of this disclosure, people are healthier, they make more response-able decisions, and relationships improve.

9 Claims, 7 Drawing Sheets

(56) References Cited

U.S. PATENT DOCUMENTS

| | | |
|---|---|---|
| 8,764,651 B2 | 7/2014 | Tran |
| 8,920,332 B2 | 12/2014 | Hong |
| 8,961,415 B2 | 2/2015 | LeBoeuf et al. |
| 9,408,545 B2 * | 8/2016 | Felix .................. A61B 5/04017 |
| 9,974,463 B2 * | 5/2018 | Rutkove .............. A61B 5/4519 |
| 2009/0099462 A1 | 4/2009 | Almen |
| 2012/0089036 A1 | 4/2012 | Felix |
| 2012/0245436 A1 * | 9/2012 | Rutkove .............. A61B 5/4519 600/301 |
| 2016/0150989 A1 * | 6/2016 | Felix .................. A61B 5/04017 600/523 |
| 2016/0367164 A1 | 12/2016 | Felix et al. |

\* cited by examiner

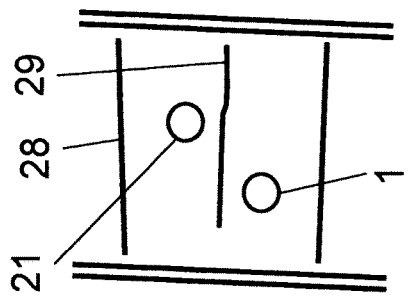
Fig. 5B
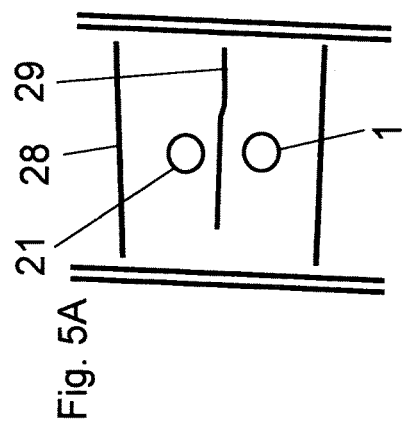
Fig. 5A
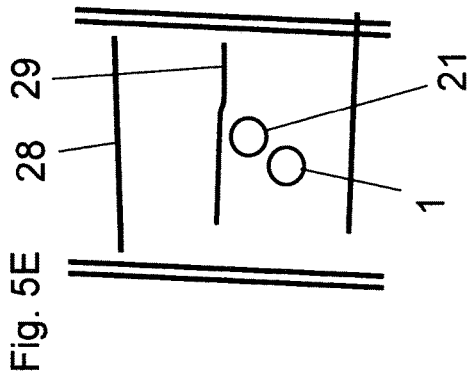
Fig. 5E
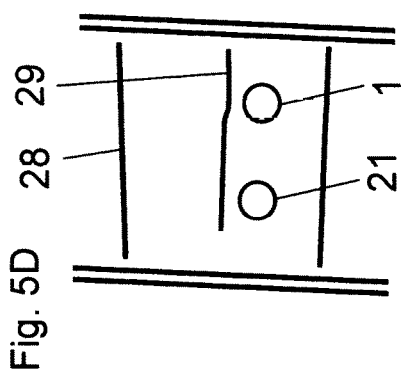
Fig. 5D
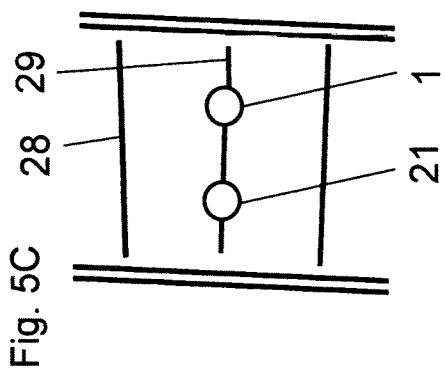
Fig. 5C
Fig. 5

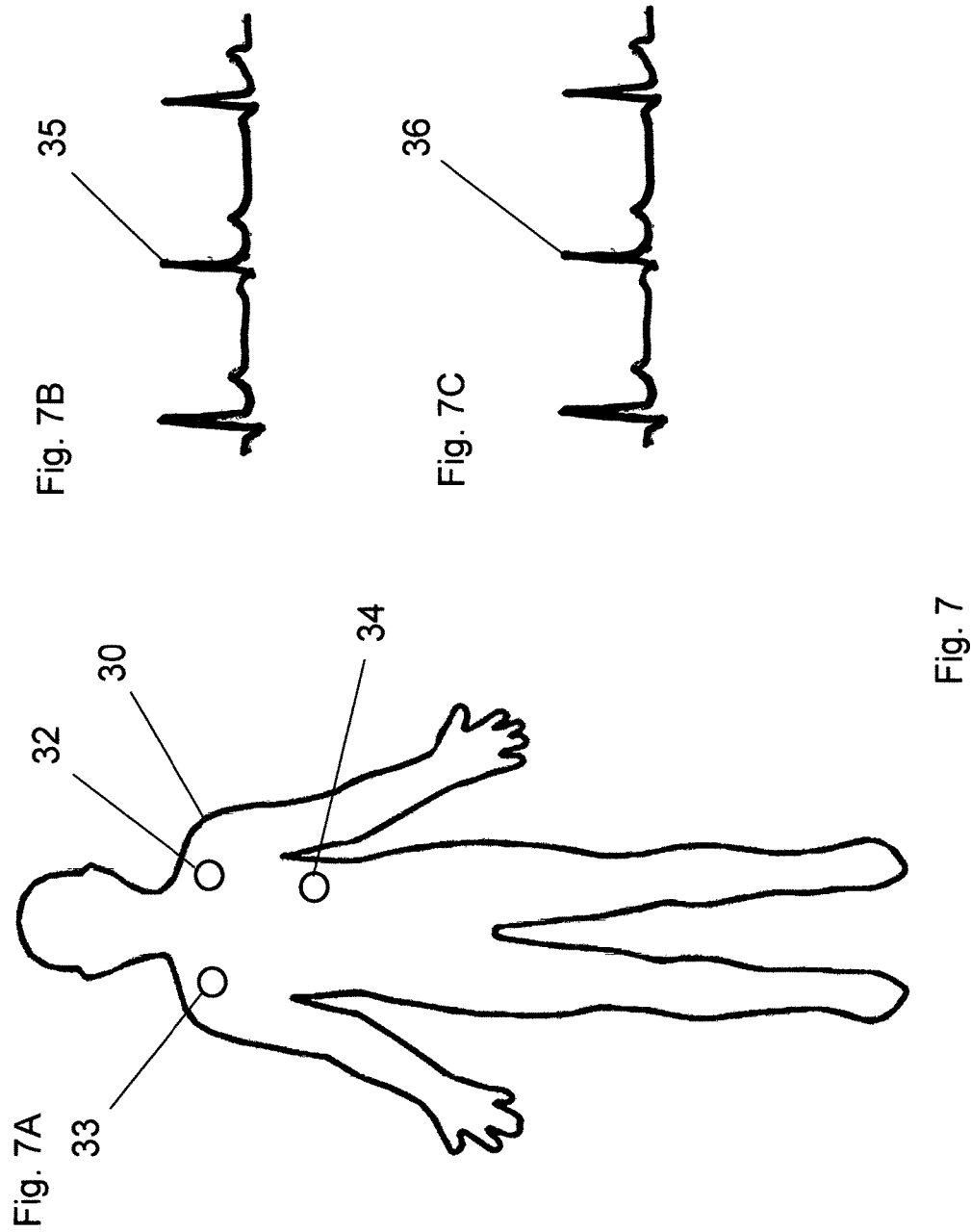

SENSING CIRCUIT WITH CASCADED REFERENCE

CROSS-REFERENCE TO RELATED APPLICATIONS

This non-provisional patent application claims priority under 35 U.S.C. § 119(e) to U.S. Provisional Patent application, Ser. No. 62/274,119, filed 31 Dec. 2015 and to U.S. Provisional Patent application, Ser. No. 62/292,486, filed 8 Feb. 2016, the disclosures of which are incorporated by reference.

BACKGROUND

Bad stress, also called distress, is a response to a stimulus that negatively disrupts our physical/mental or emotional environment. A stressful event has multiple consequences for our physiology, the main being the "fight or flight" response. Epinephrine, more commonly known as adrenaline, is a hormone secreted from the adrenal glands, which are near the kidney in the human body. When people feel emotions such as fear (any type including freeze, faint, flee and fight) or anger, this causes adrenaline to be released into the bloodstream, which causes an increase in heart rate, muscle strength, blood pressure, and sugar metabolism. The "flight or fight response" prepares the body for strenuous activity. Adrenaline is found in tiny amounts in the body, in amounts that vary from individual to individual; it is essential for maintaining the heart because of its ability to divert blood to tissues under stress. Constant adrenaline production through ongoing or repeated stress, however, triggers a chronic stress response in the body leading to cortisol production, and an elevated level of cortisol in the body has been shown to lead to disease. Exposure to chronic stress induces various physical, emotional and mental results that can ultimately lead to disease. Stress-related disease is a global health problem that costs the US economy $190B each year. There is a great need in the art for recognizing, decreasing and minimizing bad stress.

Another aspect of stress is good stress. As used herein, eustress means beneficial stress—either psychological, physical (e.g., exercise) or biochemical/radiological (hormesis). The term was coined by endocrinologist Hans Selye, consisting of the Greek prefix eu-meaning "good" and stress, literally meaning "good stress." Typically the stress referred to in this document is bad stress.

As is known in the art, the most optimal level of stress is a minimum of bad stress and an amount of eustress. There is a need in the art for optimizing the quantities and qualities of stress experienced, in a way that is customizable for each person.

For example of societal cost related to stress, 60-80% of primary care doctor visits are related to stress, yet only 3% of patients receive stress management help. Big and little stresses can cause similar metabolic cascades in the body. Little stresses are not irrelevant. When we feel stressed, we are reactive, and we don't have access to all our intelligence and brain capacity for making conscious choices. Instead we become defensive. People can also become numb to stress and not realize the impacts to them on their body and in their lives and work. The best ways to address stress and its impacts are to notice stress in the moment and take actions: to stop the increase of stress that is happening; to decrease the amount of stress experienced during regular repeated events; to decrease the quantity, duration and intensity of stressful events one experiences; and to learn ways to decrease one's stress baseline. This can be achieved by learning calming methods and by making different decisions to avoid stressful scenarios. There are needs in the art for noticing stress in the moment and providing real-time feedback about the amount of stress experienced above a previous state or a control comparison state.

Most stress occurs during everyday activities, hence stress needs to be measured throughout a person's normal routine. Some devices known in the art can measure stress in artificial settings, such as with lie detector tests and biofeedback machines. Such devices in real life applications need to be convenient and more accurate—as this yields higher efficacy.

People need to be alerted to stress when it occurs so changes can be implemented quickly to alter their physiological state immediately. This also allows gradual learning of new patterns and allows implementation of new enhanced responses, perhaps eventually with no reminder or alert system.

Recently there has been a great rise in the use of wearable devices. This began in the medical industry and then subsequently spread to the fitness industry. This interest has expanded to include many aspects of health. There has been a desire in the field to measure heart rhythms with wearable devices since people want direct feedback about their body as they go about life activities. New technology has allowed smaller, longer lasting devices that are practical for everyday use. Real-time monitoring and feedback is motivating—people are competing to better themselves and against others as motivation. The signals in extremities, such as the wrist, where wearables are often placed, are smaller and more subtle than on the trunk of the body nearer the heart, so the wearable device must be more sensitive. Wearables also need to be low power so that people can wear them for extended periods without recharging.

Relevant wearable devices known in the art include:
1) FITBIT TRACKER is advertised as using a three-dimensional accelerometer to sense user movement (steps taken, distance walked, calories burned, floors climbed and activity duration and intensity). It also is described as measuring sleep quality by tracking periods of restlessness, how long it takes the wearer to fall asleep and how long they are actually asleep.
2) SPIRE is described as using sensors with algorithms to sense activity and breathing patterns. These sensors are said to detect the respiratory movement when worn on a belt clip type apparatus by measuring expansion and contraction of abdominal and/or thoracic cavities. With the SPIRE MIND and BODY TRACKER and companion app on an iPhone, one supposedly can become more mindful and calm throughout the day. It clips to pants or a bra, and the tiny Spire Stone is said to sense respiratory patterns to detect changes in one's state of mind (Tense, Calm, and Focus). With gentle notifications, insights, and breathing exercises, Spire is said to unlock a more mindful, balanced, and productive day. One's state of mind affects how one breathes. But how one breathes can also change one's state of mind. For example, studies have uncovered how slow, deep and consistent breathing can lower blood pressure, reduce stress, and increase the flow of endorphins in the blood stream. Spire is said to notify via an app on the iPhone or iPad when the wearer is tense, needs to take a deep breath, has just experienced an extended streak of calm, and other functions.
3) PEBBLE device has a programmable CPU, memory, storage, Bluetooth, a vibrating motor, a magnetometer, an ambient light sensor, and an accelerometer working in concert to provide biofeedback data to the user.

4) GOOGLE WATCH prototype is said to continuously measure biometric data including pulse rate and skin temperature and to analyze fine motion, including gait and balance. The watch is described as also measuring ambient temperature, noise and light, as well as altitude, which help to provide context for the biometric data.

5) APPLE WATCH is described as equipped with heart rate measuring circuits, which uses infrared and visible-light LEDs and photodiodes.

6) MICROSOFT BAND, released in 2014 (and 2nd edition in 2015) is described as having the following features: GPS, Ambient light sensor, UV sensor, Skin temperature sensor, Capacitive sensor, Galvanic skin response sensor, and Barometer.

Some wearables are now attempting to measure and address a user's emotional states.

7) The WELLBE bracelet is said to monitor a person's heart rate using a patent-pending algorithm to determine their stress and calmness levels based on time, location and people met throughout your day. Crafted from cork, the WellBe bracelet is advertised as light-weight, durable, and soft against skin.

8) FEEL.CO is shown to have four integrated sensors on a wristband and said to monitor a variety of physiological signals such as, electrodermal activity, blood volume pulse, and skin temperature, while proprietary algorithms in the background are said to translate those bio-signals into emotions.

9) ALTRUIS, designer wearable technology by VINAYA, is said to filter a person's smartphone notifications to improve their digital balance, so a person stays connected, not distracted. It is a jewelry-based activity tracker by London-based Vinaya that comes in a ring or necklace format.

10) The PIP is a small handheld wearable fitness device that is said to track stress through the skin and couple with game technology to encourage people to relax. It is not wearable in the typical way—one carries it and must pause from normal activity to put one's thumb(s)/finger(s) on it. Two games are available on the app—one in which the user helps turn a landscape from winter to summer and another where the user races a dragon against a peer (the less stressed person wins). A person's stored stress stats are said to be available too, but the focus of this product appears to be making stress relief fun. It is said to achieve this by detecting variations in electrodermal activity (EDA). The skin pores on fingertips are said to be extremely sensitive to changing levels of stress. Pip supposedly accurately captures these changes and, through biofeedback, allows a user to visualize them.

11) OLIVE is said to analyze patterns and biological indicators by continuously monitoring the complexity of a person's stress behind the scenes to help them build awareness of their body's stress response. Everyone's stress is different. Supposedly Olive gets to know how stress is triggered. This product is not yet in production.

12) NEUMITRA is said to have embedded proprietary biomodules help measure and manage the autonomic nervous system. The product is said to provide a real-time autonomic score, assessing physiology and its interaction with movement and temperature. The biomodules are said to be encased in a design that seamlessly blends into daily life, allowing a person to take advantage of understanding their brain health every minute of every day 13) The LIEF is an ultra-thin biosensing patch that is said to measure heart and breath. Lief is said to teach control over a person's natural stress response through gentle, safe biofeedback exercises. It is said to reduce triggered responses so one stays mindful and in control throughout the day.

14) ZENSORIUM is marketed as a wearable fitness monitor that differentiates good stress from bad stress, tracks activity with heart rate sensing, and provides advanced sleep science insights with REM/NREM. Zensorium Being is said to map mood into four different zones, differentiating good from bad stress. It is said to sense energy, heart rate and changes in blood pressure, and determine emotions from heart rate variability. Supposedly capable of continuous monitoring, it claims to know when a wearer is stressed and provides steps for deep breathing exercises to reduce stress. This same company also makes Tinke, a device attached to the iPhone that is said to monitor stress and blood oxygen saturation by measuring heart rate, respiratory rate, blood oxygen saturation and heart rate variability to determine fitness and stress indices.

15) JAWBONE is a world-leader in consumer technology and wearable devices, building hardware products and software platforms powered by data science. Jawbone's UP® system is said to help people live better by providing personalized insight into how they sleep, move and eat. The company's approach to lifestyle tracking may be relatively unique, with over 600 patents granted or pending related to its ecosystem and wearable technology manufacturing processes. Jawbone is also the creator of the best-selling JAMBOX® family of wireless speakers, the award-winning Jawbone ERA® Bluetooth® headsets, and NoiseAssassin® technology. Headquartered in San Francisco with offices globally. Their products are said to measure Heart rate, Respiration and Galvanic Skin Response (GSR) combined with a Tri-axis accelerometer. The Jawbone products typically use optics for measurements. Their best product appears to have 4 electrodes, is said to require the user to be still during measurements, and measurements can only be obtained about every hour, not continuously. It is said to measure heart rate upon waking and then passively at regular intervals through the day by measuring electrical properties in the skin. Their products also use a lot of power.

16) KARDIA was developed by AliveCor, Inc., a privately held company headquartered in San Francisco. They produce a band which they claim allows people to take control of their heart health through the use of innovative mobile health solutions including Kardia Mobile, Kardia Band, the AliveCor app and Kardia Basic and Premium heart care services. A wristband is supposedly used to provide an ECG to medical providers, for use for conditions such as Atrial Fibrillation, a common heart condition. It is unclear how many electrodes are used in their style device, often 4 or more. The technology appears basic and uses an optical sensor to provide information.

17) Two new upcoming products that are not yet on the market are the SENCEBAND and SENCEHUB, which are described on kickstarter. SenceBand is said to accurately measure ECG signals from one wrist. Sence-Hub is said to turn those raw ECG signals into emotional insights.

SenceBand's ECG Tracking from One WristSenceBand is said to measure ECG using a patent-pending technology that allows it to cancel out the electromagnetic "noise" from the wearer's body. This mechanism is said to filter out things like electrical signals from muscle contractions and leave only the electromagnetic feed from the heart (ECG). This filtering method is said to allow SenceBand, a smart bracelet, to measure ECGs from one wrist. It claims that it is capable of detecting up to 64 emotions from placing the HRV into an algorithm contained within the ScenceHub software. The Sence wristband is transmitted to a Cardio-Cloud service, also developed by Platform 20K, and is said to continuously monitor. This service is offered to any medical professional to analyze and store cardiovascular data from any internet-enabled cardiograph. It is unknown if Sence products are able to do what they claim nor what technology is used, as products are not yet on the market, and there is not much product documentation available.

The detailed hearth rhythms detectable by non-wearable ECG medical products have never before been detectable with wearable devices.

There are currently no wearable devices for sale on the market that are convenient for everyday life activities that accurately and continuously measure stress, with the accuracy of medical devices. Some devices known in the art for detecting stress attempt to do so by extracting HRV and pulse derived typically from ECG by plethysmography. Some products attempt to measure ECG using optics, which requires much more power. Attempting these methods requires larger and heavier equipment and/or so much power that devices are not practical for everyday activities, they can't measure continuously, therefore they are not as efficacious and need to be recharged frequently.

SUMMARY OF THE INVENTION

Embodiments of the methods, wearable devices and systems of this disclosure may be useful for accurately sensing and alerting a user to changes in their stress and amount of relaxation during daily activities, using little power. In one embodiment, the wearer is provided with a way to notice their changes in stress level, and if it is increasing, they are optionally prompted to take actions to 1) prevent reacting from a distressed/stressed/triggered state, 2) promptly engage in de-stressing behaviors, 3) identify and increase relaxation behaviors, and 4) identify chronic triggers and take actions to decrease reactivity and/or exposure to these events thus decreasing the adrenaline and cortisol being produced in their body.

Embodiments of the devices, methods and systems of this disclosure may be worn discretely and provide real-time feedback that can be used to assist people in enhancing their own awareness of their physiological states and related emotional states. People can learn their personal early warning symptoms that indicate rising stress levels. People can learn to identify internal and external triggers of distress. The devices, methods and systems of this disclosure provide feedback to facilitate learning techniques (e.g., breathing, meditation, thought-stopping, etc.) for calming oneself down and triggering a relaxation response.

Embodiments of the devices, methods and systems of this disclosure are useful for measuring electrovesselgram (EVG) and subdermal spectrogram (SSG) of a wearer/user, using a method that is sufficiently accurate even far away from the heart, such as on a wrist or other appendage. There are no devices, methods and systems known in the art that measure EVG or SSG. In embodiments of this disclosure, EVG and SSG are measured simultaneously, about simultaneously, in either sequence and/or at different times.

Embodiments of the devices, methods and systems of this disclosure create and use a cascaded reference, an arbitrary reference and/or a noisy reference to cancel out ambient and system noise with little power, making a long-lasting device that produces accurate data. In an embodiment, an arbitrary reference and a noisy reference are cascaded together. This unique reference and sensing configuration allows detection of physiological stress indicators in a way that is potentially convenient, low power and non-invasive resulting in higher levels of use, follow-through with recommendations, and ultimately impact.

BRIEF DESCRIPTION OF THE DRAWINGS

FIGS. 5A-5E show illustrated examples of how the circuits of this disclosure may be configured to be electrically connected to a specimen, in this instance a human wrist (28).

In FIG. 6A, an illustrated specimen (30), a human wearer, is wearing a device of this disclosure (31) on their wrist (28), and FIG. 6B shows a scaled up representation of this region.

FIGS. 7A-7C show illustrated examples of a specimen with leads (7A) and waves (7B-C). FIG. 7A shows an illustration of a specimen (30) with leads (32, 33, 34) attached, FIG. 7B shows a typical ECG waveform produced, and FIG. 7C shows an output waveform (36) that is being recorded using a device of this invention.

DETAILED DESCRIPTION OF THE INVENTION

Figure 1:
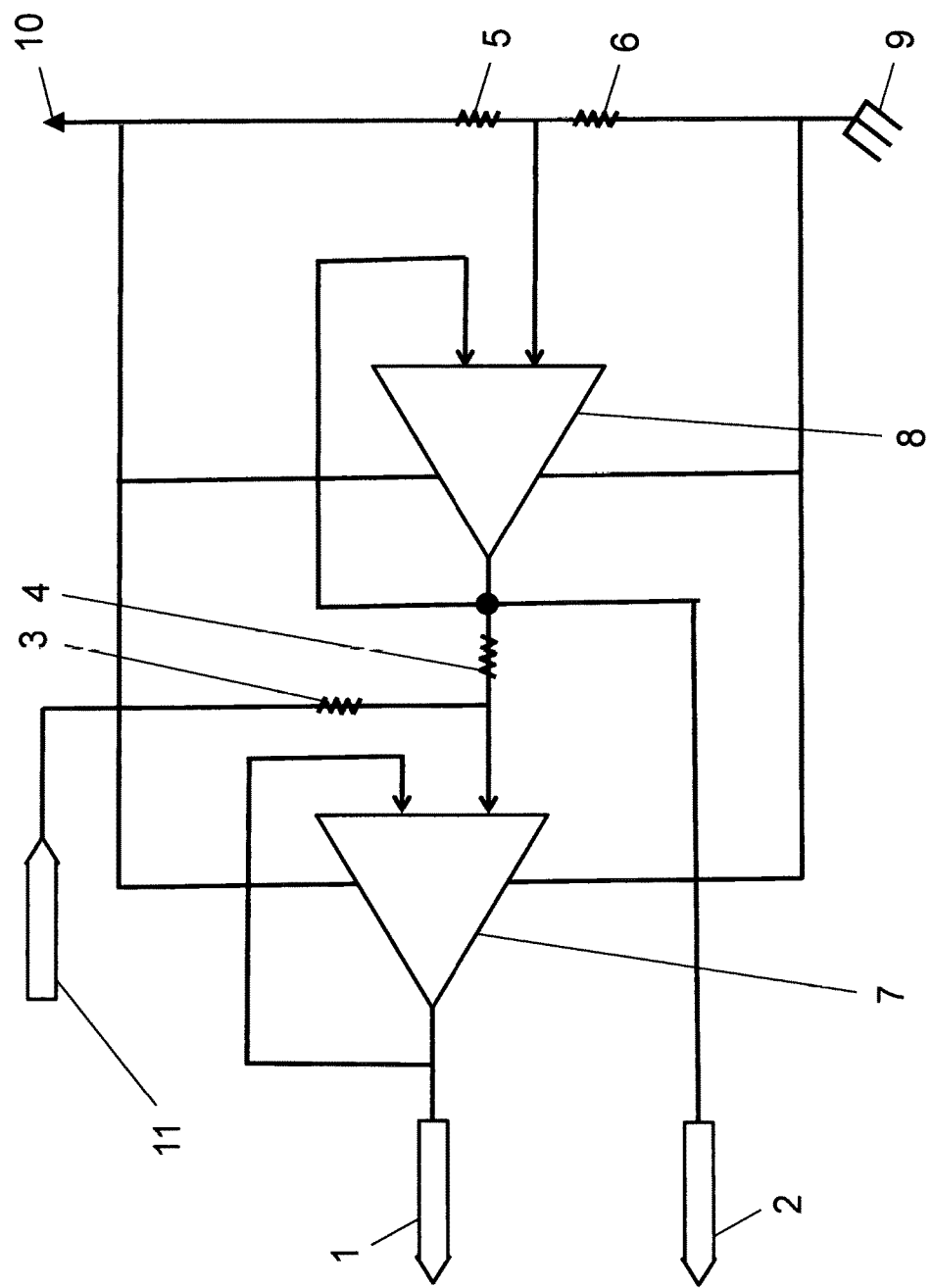
FIG. 1 shows an illustrated example output of a cascaded reference (1) and an output of the noisy reference (2).

Non-limiting and non-exhaustive embodiments of the invention are described with reference to the following figures, wherein like reference numerals refer to like parts throughout the various views unless otherwise specified.

The drawing elements are as follows:

| | |
|---|---|
| 1 | Reference output |
| 2 | Reference output |
| 3 | Resistor |
| 4 | Resistor |
| 5 | Resistor |
| 6 | Resistor |
| 7 | OpAmp |
| 8 | OpAmp |
| 9 | System ground |
| 10 | Positive voltage rail |
| 11 | Arbitrary signal input |
| 12 | Resistor |
| 13 | Resistor |
| 14 | Capacitor |

| | |
|---|---|
| 15 | Resistor |
| 16 | Capacitor |
| 17 | Resistor |
| 18 | Capacitor |
| 19 | OpAmp |
| 20 | OpAmp |
| 21 | Receiving electrode |
| 22 | Signal output |
| 23 | Cascaded reference circuit |
| 24 | Filtering and amplifying circuit |
| 25 | Microcontroller |
| 26 | Optional accessories |
| 27 | Analog front end |
| 28 | Wrist |
| 29 | Blood vessel |
| 30 | Specimen |
| 31 | Device for assessing stress |
| 32 | LA electrode location |
| 33 | RA electrode location |
| 34 | LL electrode location |
| 35 | Typical lead II ECG Waveform |
| 36 | R wave segment |

FIG. 1 shows an example output of a cascaded reference (1) and an output of the noisy reference (2), in accordance with an embodiment of the disclosure.

The pair of resistors (5, 6) divides the voltage between system ground (9) and positive voltage rail (10) in half to form an unamplified noisy reference that is also a voltage divider. Choosing approximately half voltage minimizes the possibility of amplifier (7, 8) saturation.

A pair of resistors (3, 4) combine two signals, the output of noisy reference amplifier (8) and the arbitrary signal (11). Typically the resistor (3) after the arbitrary signal input (11) is large, in an embodiment about 10M Ohms. The resistor (4) after the noisy reference amplifier (8) typically is more likely to be small, in an embodiment about 10-100 Ohms. Together these make scaled resistors and this resistor pair (3, 4) is a mixing circuit that optionally combines the two signals in different proportions as selected.

The other pair of resistors (5, 6) makes a noisy reference that is about half of the system voltage. The amplifier (8) is in a unity gain configuration, and this amplifies the current of the signal without changing the voltage. The signal comes out of amplifier (8) and is mixed with the arbitrary wave signal (11) through the pair of resistors (3, 4) which is then provided to amplifier (7) in a unity gain configuration. Amplifier (7) amplifies the current of the signals fed through the pair of resistors (3, 4), but does not amplify the voltage, and provides this for output into a specimen and/or the amplification and filtering circuits. The noisy reference (2) is optionally output for use in the amplification and filtering circuits.

Ground (9) is optionally a system ground, a chassis ground or other equivalents known in the art. When the system is used as a wearable device for real-time feedback during everyday activities, the ground (9) is not an earth ground.

Figure 2:
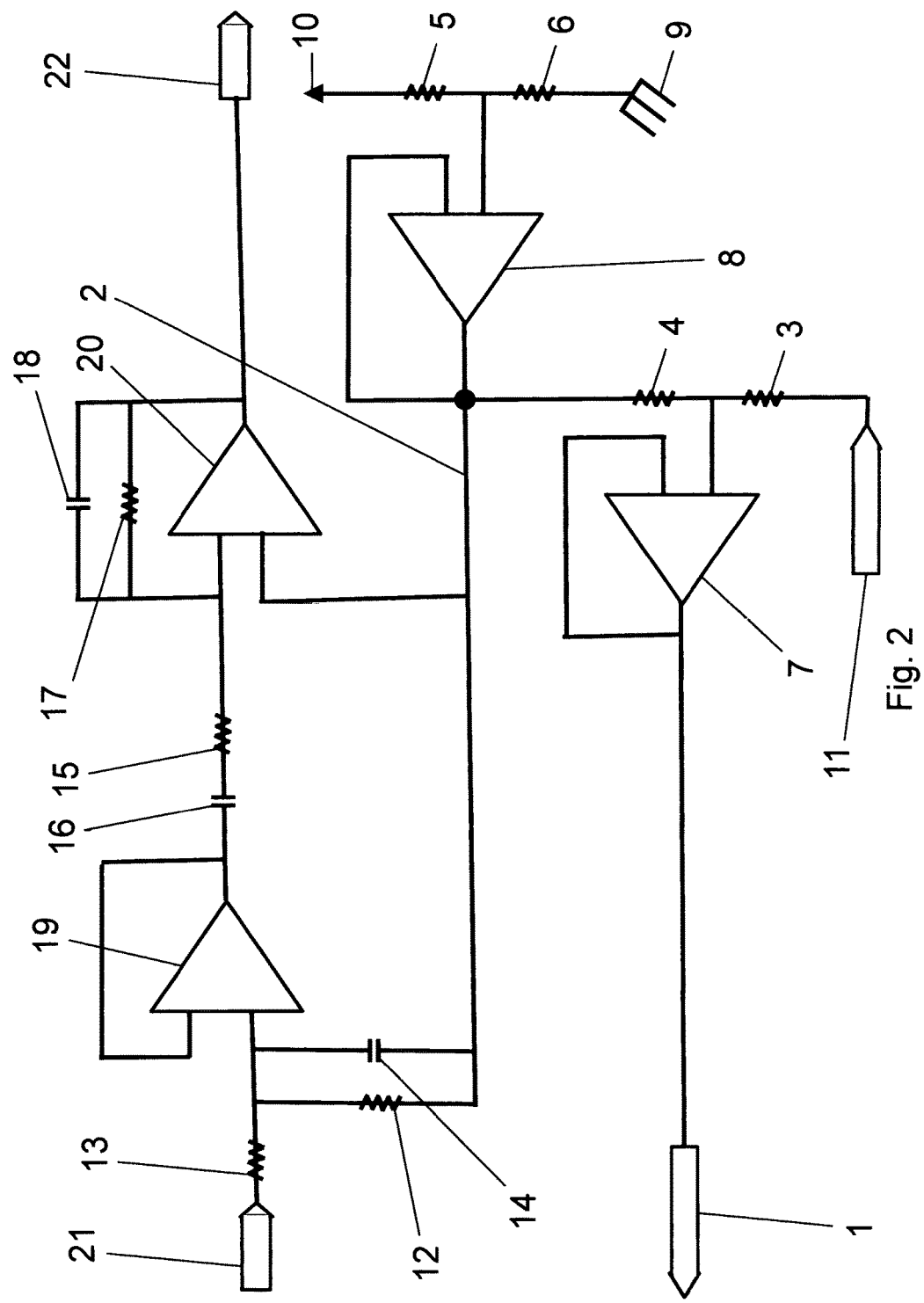
FIG. 2 shows illustrated example resistors (12, 13) and capacitor (14) combine to create a low pass filter.

FIG. 2 shows how example resistors (12, 13) and capacitor (14) combine to create a low pass filter, in accordance with an embodiment of the disclosure. Typically resistor (12) is very large, in an embodiment about 100K to 100M Ohms. Typically capacitor (14) is very small, in an embodiment about 100-10,000 pF. Typically the value of resistor (13) is medium, in an embodiment about 10-100K Ohms, in an embodiment 30K Ohms.

Resistors (15, 17), capacitors (16, 18) and amplifier (20) combine to produce a high pass filter. The circuit is configured so that the filtering frequency is most strongly controlled or influenced by capacitor (16).

Resistors (15, 17), capacitor (18) and amplifier (20) combine to form a low pass filter. The circuit is configured so that the filtering strength and frequency are mostly controlled or influenced by resistor (17) and capacitor (18).

Resistors (15, 17) and amplifier (20) combine to form a voltage amplifier.

In an embodiment, the circuit is configured so that the two low pass filters (12, 13, 14 and 15, 17, 18, 20), the high pass filter (15, 16, 17, 18, 20) and/or the voltage amplifier (15, 17, 20) function about simultaneously. Optionally the voltage amplifier (15, 17 and 20) is configured as an inverting amplifier.

In an embodiment, some of the signal from the cascaded reference is output (2) into the amplifying and filtering circuit (12-20), as shown in FIGS. 1 and 2.

In FIG. 2, a signal is applied to or sensed by a receiving electrode (21) from a specimen. This enters the first low pass filter circuit (12, 13, 14). An amplifier (19) in a unity gain configuration amplifies the current of the signal but not the voltage. The signal is high pass filtered (15, 16, 17, 18, 20) to remove, in an embodiment, DC offset, baseline wander and/or low frequency noise. The signal is then low pass filtered (15, 17, 18, 20), in an embodiment, to remove muscle noise and other unwanted signals. The voltage of the signal is amplified (15, 17, 20). The amplified and filtered signal that was originally sensed or received by the electrode (21) is then sent to an output (22). Essentially, the devices of this disclosure are configured, in an embodiment, to cancel out interference because noise from an unamplified noisy reference or voltage divider is injected into the specimen, making the signals from the specimen become essentially the same order of magnitude as the noise in the components that measure and analyze that signal, so the small specimen signals are now distinguishable.

Figure 3:
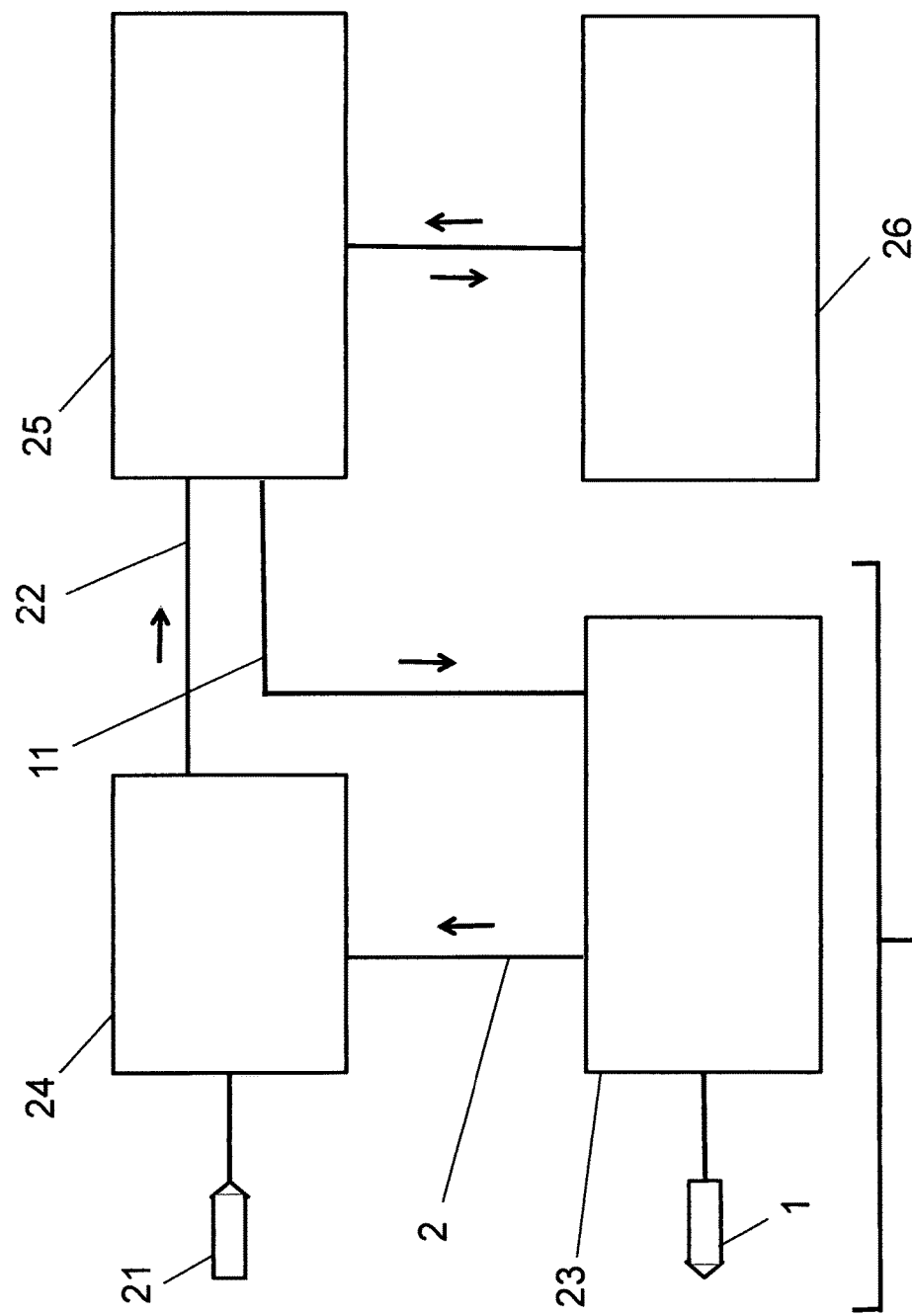
FIG. 3 shows an illustrated example system in which a microcontroller (25) is used for optionally storing, processing, or analyzing data, etc.

FIG. 3 shows an example system in which a microcontroller (25) is used for optionally storing, processing, or analyzing data, etc., in accordance with an embodiment of the disclosure. Instead of a microcontroller (25), in other embodiments this could be a system on chip (SoC), a complex program and logic device (CPLD), an application specific integrated circuit (ASIC), a fully programmable gate array (FPGA), or other equivalents known in the art.

Optional accessories (26) are shown in FIG. 3, such as a transmitter, computer for storage, a cell phone for display, etc.

FIG. 3 shows the noisy reference output (2) going to the filtering and amplifying circuit (24).

Figure 4:
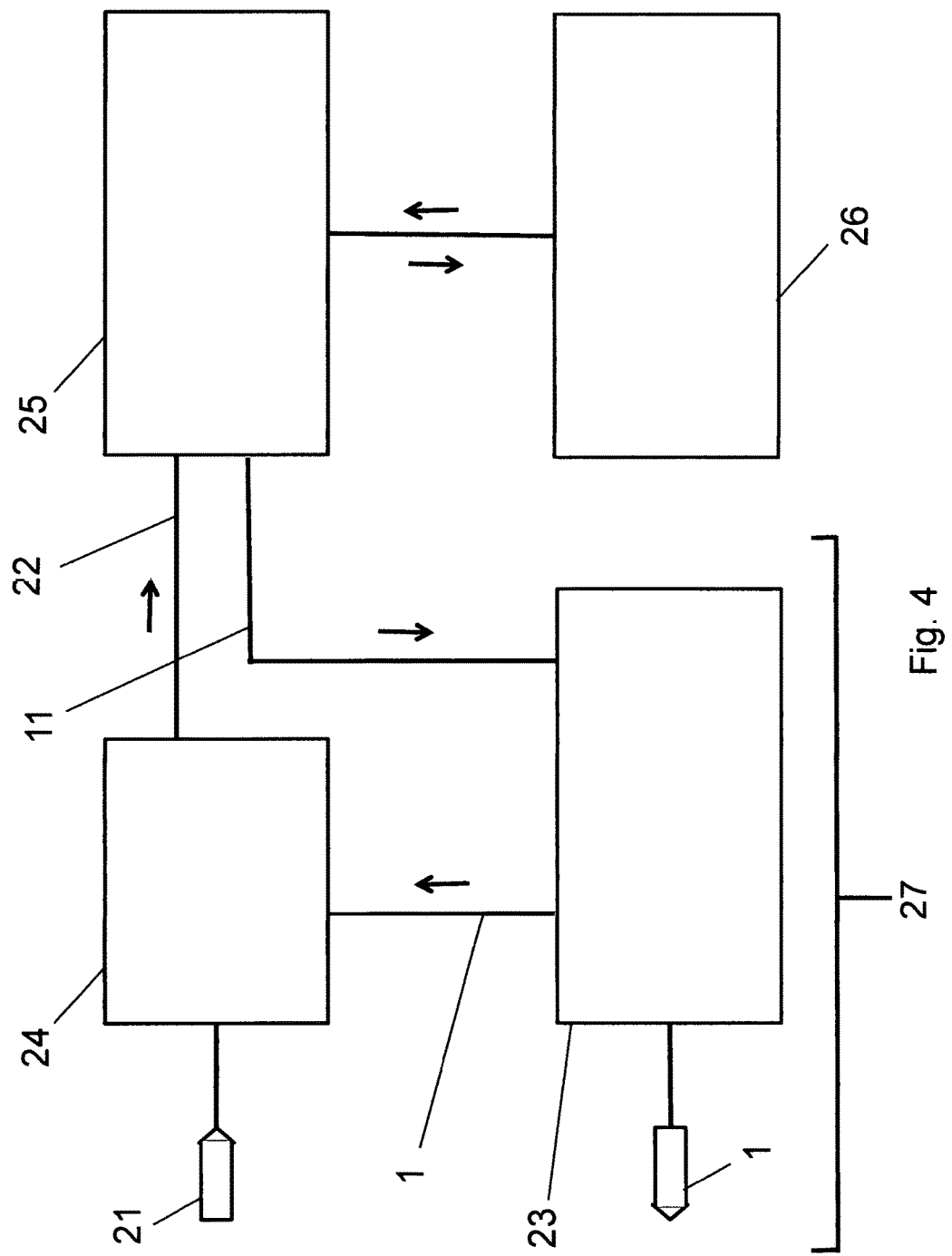
FIG. 4 illustrates an example output (1) of a cascaded reference (23) going to a filtering and amplifying circuit (24).

FIG. 4 illustrates an example output (1) of a cascaded reference (23) going to a filtering and amplifying circuit (24), in accordance with an embodiment of the disclosure.

In FIGS. 3 and 4, the analog front end (27) delivers to and receives signals from a specimen. In one embodiment, that specimen is an organism.

In FIGS. 3 and 4, the arrows represent the direction that the signal travels through the system.

In this embodiment, the arbitrary signal (11) is generated by the microcontroller (25) or equivalent and is delivered to the cascaded reference circuit (23) and through the output (1) into a specimen. Signal from the specimen is picked up through the input (21) and delivered to the filtering and amplifying circuit (24) and delivered to the microcontroller (25). A reference signal, such as the noisy reference (2) shown in FIG. 3 or the cascaded reference (1) shown in FIG. 4, is also delivered to the amplifying and filtering circuit (24). Signal from the microcontroller (25) is optionally delivered to accessories (26) for further storage, analysis, display, etc.

The organization and order of the elements can be changed in ways that are known in the art of electronics to enable sufficient filtering, amplifying, and/or referencing, etc.

FIG. 5 shows five examples of how the circuits of this disclosure may be configured to be electrically connected to a specimen, in this instance a human wrist (28). Five optional configurations (A-E) are shown for having the signal output (1) and receiving electrode (21) proximal to a blood vessel (29) in a wrist (28). In FIG. 5A, the electrodes (1, 21) are approximately adjacent to the blood vessel (29) approximately in line with each other on either side. In FIG. 5B, the electrodes (1, 21) are diagonally opposed from each other, on either side of the blood vessel (29). In FIG. 5C, the electrodes (1, 21) are in line with and over the blood vessel (29), configured to be electrically connected to the skin by methods known in the art. In FIG. 5D, the electrodes (1, 21) are in line with each other and offset longitudinally (or laterally) from the blood vessel (29). In FIG. 5E, the electrodes (1, 21) are longitudinally offset and laterally offset on one side of the blood vessel (29). While the configuration shown in FIG. 5E may not be preferred, it is possible.

Figure 6:
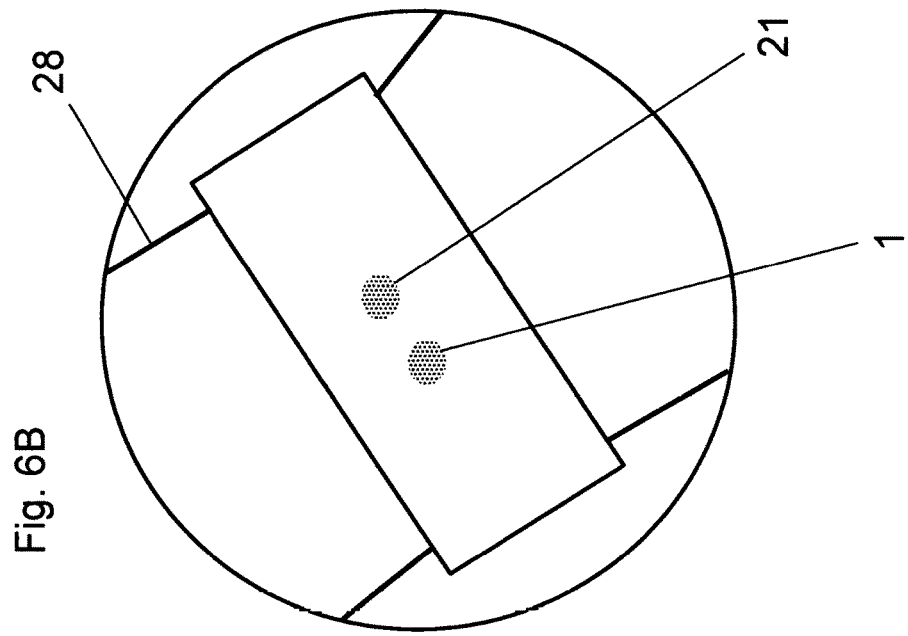
FIGS. 6A-6B show illustrated examples of a human wearing a device (A) and a scaled up representation of this region (B).
Figure 6:
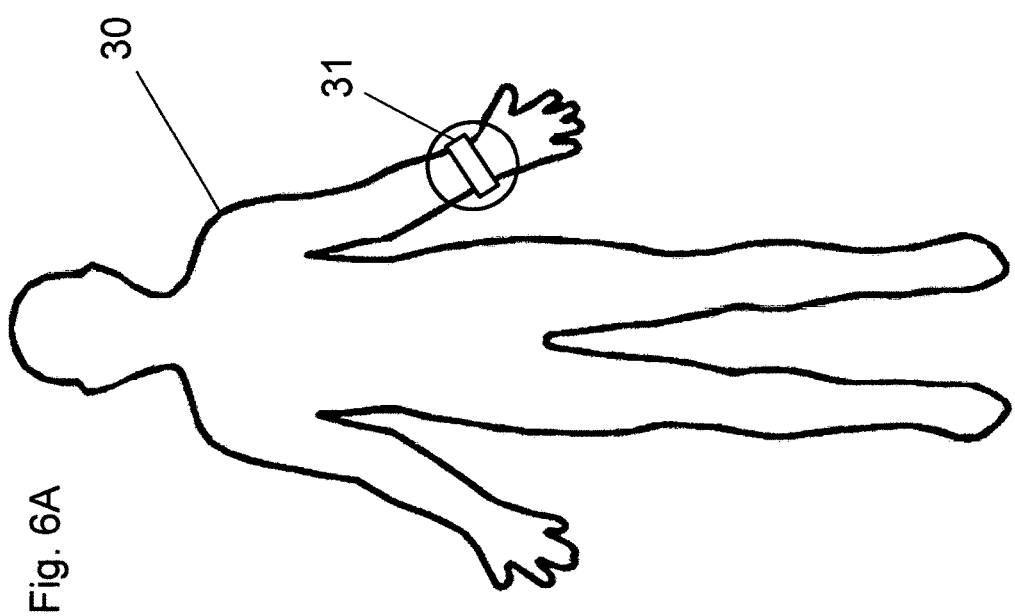

In FIG. 6A, a specimen (30), a human wearer, is wearing a device of this disclosure (31) on their wrist (28), in accordance with an embodiment of the disclosure. FIG. 6B shows a scaled up representation of the region with the two electrodes (1, 21) marked in hatching where they are not visible on the inside part of the device (31). Although not visible, the electrodes (1, 21) are positioned so that they will be proximal to one or more blood vessels (29) in the wearer's wrist (28).

In FIG. 7A, a specimen (30) has leads (32, 33, 34) attached for measuring ECG in a Lead II configuration), in accordance with an embodiment of the disclosure. The negative lead (33) on the shoulder of the right arm is attached first followed by the positive lead (34) on the pelvis section going to the left leg. The ground lead (32) is on the shoulder going to the left arm. FIG. 7B shows a typical ECG waveform produced from Lead II in FIG. 7A. FIG. 7C shows an output waveform (36) that is being recorded using a device of this disclosure that has two electrodes on a wrist, such as shown in FIGS. 6A-B.

An ECG or "electrocardiogram," is used to visualize heart rhythms Different ECG waveforms can be detected when electrodes are placed on different parts of the body. An ECG device measures the heart's electrical activity and displays it as a waveform. ECG devices are designed to show the sequence of depolarization and repolarization of the heart muscle.

If a wavefront of depolarization travels towards the electrode attached to the +(positive) input terminal of the ECG amplifier and away from the electrode attached to the—(negative) terminal, a positive-going deflection will result. If the waveform travels away from the +(positive) electrode towards the—(negative) electrode, a negative-going deflection will be seen. If the waveform is travelling in a direction perpendicular to the line joining the sites where the two electrodes are placed, no deflection or a biphasic deflection will be produced. Einthoven's triangle is an imaginary formation of three limb leads in a triangle used in electrocardiography, formed by the two shoulders and the pubis. The shape forms an inverted equilateral triangle with the heart at the center that produces zero potential when the voltages are summed.

Examples of electrode placements: Lead I, Lead II, Lead III:
Lead I—Left arm (+), right arm (−)
Lead II—Right arm (−), left leg (+)
Lead III—Left arm (−), left leg (+)

Cells maintain a slight imbalance between potassium and sodium ions inside and outside the cell, and this imbalance causes the generation of an electrical charge, which leads to the contraction and expansion of heart cells. This causes synchronized contraction and expansion of cells in unison through the heart muscle.

Cardiac action potentials are generated as follows:

The concentration of $K^+$ ions inside cells is about 10 times that in the extracellular fluid, whereas the concentrations of $Na^+$ and $Cl^-$ ions are much higher outside the cell than inside; these concentration gradients are maintained by $Na^+/K^+$ ATPases with the expenditure of cellular energy. The resting potential is determined mainly by the movement of $K^+$ ions across the membrane.

In the generation of the cardiac action potential, stimulation of the cell by neurotransmitters or by sensory receptor cells partially opens channel-shaped protein molecules in the membrane. Sodium diffuses into the cell, shifting that part of the membrane toward a less-negative polarization. If this local potential reaches a critical state called the threshold potential (measuring about −60 m V), then sodium channels open completely. Sodium floods that part of the cell, which instantly depolarizes to an action potential of about +55 m V. Depolarization activates sodium channels in adjacent parts of the membrane, so that the impulse moves along the muscle fiber.

The P wave shows the depolarization of the atria in the heart. Different disease states can be detected by changes in the P wave, so the details of the P wave indicate heart health.

The R wave is typically the highest amplitude waveform segment, often used to measure beats per minute in patients without atrial fibrillation. Each segment of the cardiac waveform is useful for detecting particular cardiac rhythm disorders and diseases. HRV, heart rate variability, is a specific analysis of the variability of R waves.

While the details above refer to the heart, similar principles apply to blood vessels as well, specifically the contraction of smooth muscle cells in a blood vessel cell wall. The process generates a much smaller voltage than what is generated by the cardiac muscle.

As blood flows through a blood vessel, cells in the wall of that vessel expand and contract. As those cells expand and contract, they generate an electric charge. The amount or quantity of electricity produced is relative to expansion or contraction as well as fatigue over time. Vascular smooth muscle contracts or relaxes to change both the volume of blood vessels and the local blood pressure, a mechanism that is responsible for the redistribution of the blood within the body to areas where it is needed (e.g., areas with temporarily enhanced oxygen consumption). The main function of vascular smooth muscle tone is to regulate the capacity of the blood vessels in the body. Excessive vasoconstriction leads to high blood pressure, while excessive vasodilation leads to low blood pressure. Arteries have a great deal more smooth muscle within their walls than veins, thus their greater wall thickness. This is because they have to carry pumped blood away from the heart to all the organs and tissues that need the oxygenated blood. The pulse of the blood flow and heart typically is detected by dextral palpation in any place that allows an artery to be compressed against a bone, such as at the neck (carotid artery), on the inside of the elbow (brachial artery), or at the wrist (radial artery). At these locations, and at all other blood vessels, electrical wavefronts are being generated by the blood vessels.

EVG is a measurement of the change of voltage over time emitted by the cell wall of a vessel and surrounding tissue as it expands and contracts. It is the differential voltage around the cell wall, which can be measured as a change in voltage in or near the specimen's/wearer's skin. EVG has specific frequency and amplitude characteristics. Devices, methods and systems of this disclosure measure changes in amplitude of EVG rhythms (indirectly correlated with heart movements and rhythms) at a narrow range of low frequencies less than about 200 Hz. In embodiments, the frequencies of EVG measured are less than 200 Hz, less than 100 Hz, less than 90 Hz, less than 80 Hz, less than 50 Hz, less than 30 Hz, or less than 20 Hz. In embodiments, the range of EVG frequencies measured is within a 100 Hz range, a 75 Hz range, a 50 Hz range, a 30 Hz range, a 20 Hz range or a 10 Hz range. In embodiments, the frequencies measured are between 50-100 Hz, 30-80 Hz, 10-60 Hz, 5-40 Hz, or 4-20 Hz.

In an embodiment, given the additional physiological characteristics to be measured (such as SSG), the devices and systems are configured to measure frequencies that are lower than about 250 Hz, about 1000 Hz, about 10 KHz, about 100 KHz, between 100-250 Hz, between 250-1000 Hz, between 1-10 KHz, or between 10-100 KHz.

Other devices, systems and methods known in the art measure characteristics such as electrocardiogram (ECG), impedance, bioimpedance, galvanic skin response, etc., however they are not sensitive enough to detect the subtle signals that the devices, systems and methods of this disclosure detect. They also use methods of detection that are prohibitively power intensive. The devices of this disclosure use about 10-100× less power compared to other related devices known in the art. No devices known in the art are able to accomplish even crude forms of detection with fewer than fewer than 3 electrodes. The devices, systems and methods of this disclosure work with fewer than 4 electrodes and/or fewer than 3 electrodes. The devices of this disclosure are effective with only 2 electrodes electrically contacting the specimen. The electrodes in the devices of this disclosure and the systems and methods that use these devices have electrodes that perform multiple functions, particularly that participate in measuring EVG and SSG. No other devices, systems and methods known in the art have electrodes that perform all the functions described in this disclosure. An example of a device of this disclosure with only two electrodes (1, 21) for electrically contacting a specimen is shown in FIG. 2. The devices, methods and systems of this disclosure are also useful with biological and non-biological specimen.

EVG measures small, local physical phenomena such as the expansion and contraction of blood vessels, such as arteries and/or veins and the surrounding tissues. ECG/EKG measures gross physical phenomenon such as heart muscle movement. In measuring SSG, the devices of this disclosure perform a conductive spectral analysis of a localized region of skin tissue, enabling simultaneous extraction of multiple biological markers and indicators. The devices, methods and systems of this disclosure use an arbitrary waveform generator enabling the system to adjust to changing tissue conditions, skin conditions and specimen/user needs. Impedance and galvanic skin response measuring techniques known in the art use pre-programmed, simple waveforms that provide limited diagnostic information. In an embodiment, the waveforms used in the devices and methods of this disclosure are not of a fixed type. In an embodiment, they are dynamically generated. In another embodiment, the arbitrary signal waveforms are preset to a specific pattern. In an embodiment, every device and system of this disclosure includes an arbitrary waveform. Use of an arbitrary waveform as a reference enables increased functionality, smaller and more subtle measurements to be made, more subtle analysis to be done, etc.

In an embodiment, the arbitrary signal is made up of many different signals, simultaneously or during a relatively short period of time. The benefit is that it provides a way to sense a greater range of physiological parameters in the specimen. In an embodiment the arbitrary signal changes randomly, changes continuously, or changes about every millisecond, about every 10 milliseconds, about every second, about every five seconds, about every 10 seconds, more often than every minute, about every minute and about every 10 minutes.

The devices, methods, and systems of this disclosure are able to measure EVG signals in ways that are passive, active or both. In the devices, methods and systems of this disclosure, SSG is measured actively, by injecting an arbitrary waveform into the patient. An arbitrary waveform is a waveform has no predefined characteristics. Arbitrary waveforms useful in the devices of this disclosure have a frequency content that does not exceed what is required by the receiving circuit and are high enough to measure the selected physiological characteristic and optionally avoid other selected physiological characteristics. The arbitrary waveform is also low enough power so as to not injure the specimen.

In an embodiment, the devices of this disclosure, and the methods and systems that use and communicate with these devices, have fewer than 4 electrodes, have 3 electrodes or have 2 electrodes. Devices known in the art for measuring the cruder characteristics of galvanic skin response or impedance rarely have fewer than 4 electrodes, and when they do, devices with fewer electrodes rely on a balanced, differential amplifier design. The traditional architecture is large, subject to interference and consumes more power. This prevents these devices from being real-time wearable and practical. In an embodiment, the devices of this disclosure, and the methods and systems using and communicating with them, use a single ended, unbalanced design. Devices known in the art have sets of electrodes that are separated, and are not used for measuring the multiple characteristics. In an embodiment, the devices of this disclosure measure EVG and SSG using 3 or fewer electrodes or with 2 electrodes. Fewer electrodes are preferred for reducing the cost of making and using the devices, for designing devices that use less power and are smaller, making them more convenient and easier for wearers/users to wear them. Using fewer electrodes is an element of the unbalanced, single ended design of the devices of this disclosure.

The devices of this disclosure, and the methods and systems that use and communicate with them, may use a microcontroller (or other processing logic such as field-programmable-gate-array "FPGA") generated open loop arbitrary signal to sense biological parameters. The arbitrary signal does not need to be based on the input signal pattern.

The circuitry of the devices of this disclosure, and the systems and methods that use and communicate with them, are designed so that the different measuring functions complement each other, meaning that they are used simultaneously for different purposes. As previously known in the art, measuring multiple parameters requires separate circuits, with separate electrodes for connecting and/or contacting with the specimen/wearer. Typically these circuits create destructive interference, requiring additional filtering elements. In the devices of this disclosure, and in the methods and systems that use and communicate with them, multiple measurements are taken over the same connection/electrode(s); these measurements coexist with each other without creating substantial interference while taking the measurements.

For example, in the embodiment shown in FIG. 2, the output (1) allows multiple measurements to be taken at input (21) without causing substantial interference between those measurements. Present at input (21) are the intentional system noise from the positive voltage rail (10), the arbitrary waveform from the arbitrary signal input (11) and the physiological parameters that are being measured. For example, resistor (15) is used in a high pass filter, a low pass filter and an amplifier about simultaneously.

Attempts to make devices detecting heart rhythms with fewer than 4 electrodes have been tried in the art. Examples include the Zio Patch and The Bardy Diagnostics Carnation Ambulatory Monitor. None of the above systems are sensitive enough to resolve the extremely small physiological signals on a human wrist such as the devices, methods and systems of this disclosure measure. Furthermore, all of the above systems lack support for the SSG subsystem.

The noise floor and the power of devices is a major factor in what determines their feasibility for measuring the characteristics measured by the devices of this disclosure. If the noise floor is too high, the device can't measure the subtle signals above background noise. The Zio claims a noise floor of 50 u V per ANSI/AAMI EC-38. The Carnation Ambulatory Monitor claims a noise floor of 25 u V. The devices of this disclosure have a noise floor lower than 25 u V, in an embodiment much lower than 25 u V, allowing detection of extremely small and subtle signals. In the unique design of devices of this disclosure, a noise floor less than 25 u V is achieved while still maintaining extremely low power consumption and small device size (e.g., fits in a wrist watch style band). In embodiments of this disclosure, the devices are configured so that the noise floor is about 25 u V, less than 25 u V, less than 24 u V, less than about 20 u V, less than about 15 u V, less than about 10 u V, less than about 7 u V, less than about 5 u V, less than 2.5 u V, less than 750 nV or less than 500 u V.

Devices for sale on the market require at least 4 or possibly at least 3 electrodes. The devices of this disclosure measure more subtle signals of SSG and EVG with fewer than 4 electrodes, fewer than 3 electrodes, and specifically with no more than 2 electrodes, including for referencing.

Some devices and systems of this disclosure, and some systems and methods that use and communicate with them, employ a cascaded reference, specifically a dual cascaded reference. Devices of this disclosure, and the systems and methods that use and communicate with them, inject an arbitrary signal into the specimen/wearer without problematically disturbing the quality of the EVG being measured. In an embodiment, the injected signal(s) do not cause harm to the specimen/wearer. In an embodiment, the injected signal(s) are generally not noticeable to the specimen/wearer.

The devices of this disclosure, and the systems and methods that use and communicate with them, use less power than related devices known in the art. The devices of this disclosure do not employ a traditional, balanced, differential front end design nor do they need to be designed to filter out many types of noise. As used herein, balanced refers to having symmetric input channels using a differential amplifier stage. In an embodiment, the devices and systems of this disclosure, and the systems and methods that use and communicate with them, do not need to or don't filter out many types of noise and do not use or have a differential amplifier stage. In an embodiment, the methods of this disclosure do not include a step for filtering out differential noise.

The devices of this disclosure, and the systems and methods that use and communicate with them, are useful for measuring EVG over a short distance or a short vector on the body of the specimen/wearer. The devices of this disclosure are useful with many delivery methods for electrically connecting to the specimen known in the art such as patches and parts surrounding the trunk or extremities. The devices of this disclosure become less effective for measuring EVG over a large area of the body, such as on opposite sides of the trunk of the body or between limbs. In an embodiment, the distance between electrodes is small enough that sufficiently subtle changes in measurements can be detected.

The devices and systems, and the methods that use and communicate with them, measure physiological changes due to blood vessel, vein, artery and/or capillary activity in a human, a mammal or in a non-mammal animal. In an embodiment, they are used with a rodent such as a mouse or rat. With some alternate tuning they can be configured to measure muscle and or other types of internal body electrical activity. The devices, systems, and methods can also be configured to detect changes in non-biological specimen and/or non-animal organisms.

In an embodiment, as the size of the circuit area in the devices of this disclosure increases, the devices are subject to more interference and more noise, which degrades the quality of the signal. The devices of this disclosure are suitable for miniaturization and typically have a circuit area less than 3 square inches. In embodiments, the circuit area is less than about 3 inches or between 2-3 inches. In an embodiment the circuit area is less than 2.5 inches, less than 2 inches or less than 1 inch. In an embodiment, the devices of this disclosure fit in a standard smart watch or smart watch band as known in the art. In an embodiment, the devices, methods and systems of this disclosure fit in and work with a third party watch and/or band such as the Pebble watch.

In an embodiment, the devices and systems of this disclosure are not designed to be connected to other devices (e.g., smart watches) for electrically connecting to the specimen that have a large circuit area or to be connected to an external power source. The devices referenced herein are designed as small, IEC type BF external, body worn, floating devices.

In an embodiment, devices of this disclosure, and related systems and methods, also include or connect with an API, an application program interface, a set of routines, protocols, and tools for building software applications. The API specifies how software components should interact with each other including for communication and programming graphical user interface (GUI) components.

The devices of this disclosure are useful for measuring sympathetic nervous system activation and offering non-invasive ways to observe effects on the vagus nerve. The cascaded reference devices of this disclosure are lower noise than previously known devices. Various noise sources are incorporated into the reference and the specimen/wearer, thereby cancelling out interference. Due to the increase in circuit simplicity, lower level, smaller and/or more subtle physiological or other specimen signals can be observed and measured. This assists in accomplishing the increased sensitivity.

An analogy to the way noise is handed in the systems and devices of this disclosure, is two people surfing, travelling on a wave of ocean water at the same time—they look like they are standing still to each other, even though they are each moving relative to the beach. This is similar to two people on two swings, swinging in the same rhythm at the same points in the cycle—to each other they appear to not be moving. The tight coupling of the device to the body allows rejection of unwanted interference even when it is present in the patient.

The devices of this disclosure are similar to the concept of using driven shields or driven guards in an isolated system in that interference is incorporated, actually injected into the system, rather than rejected. Power supply noise or another other type of noise is injected into the system, not filtered out.

The circuits of the systems of this disclosure inject interference from aspects of the system, thereby cancelling out this interference in the measurements and analysis of the desired signal.

A cascaded reference has never been used or considered useful in ECG or related devices, to the knowledge of the inventors.

The devices of this disclosure are able to add an arbitrary signal as part of the cascade. The benefit of adding an arbitrary signal is the ability to sense additional physiological parameters by injecting a signal and monitoring how it is modified by the physiological processes within the body.

An arbitrary wave, as known in the art, is a computer-generated wave that is defined by an array of values. More spectra and corresponding responses can be observed in a shorter amount of time using an arbitrary wave. The arbitrary waveform is selected based on desired phenomenon to be measured.

In an embodiment, in the devices of this disclosure, the cascaded reference output includes an arbitrary signal and noise from the circuitry, power supplies and/or received interferences.

In an embodiment, there is no feedback loop from the input to the internal arbitrary waveform generator.

In an embodiment, one electrode picks up (senses) what the specimen/wearer generates superimposed upon the specimen-modified arbitrary signal. The reference signals are injected into the specimen or organism, and the specimen or organism modifies and changes one or more of the reference signals, and it is specifically this modification that the circuits and methods of this invention are designed to detect and measure. These one or more modifications provide information about the specimen or organism. It is similar in some ways to the how a sound signal is bounced or reflected off of a specimen to produce an echo, however the reference signals travel through or along the specimen or organism before being detected or sensed by the sensing electrode of the circuit.

In the devices and systems of this disclosure, when the specimen/wearer changes state, the arbitrary signal that is detected measurably changes, and the specimen's/wearer's changed physiological parameter is quantified.

In an embodiment, measurements of specimen/wearer SSG and EVG are recorded over time. In an embodiment, measurements of specimen/wearer SSG and EVG are compared to a standard baseline or that type of specimen/wearer. In an embodiment, measurements of specimen/wearer SSG and EVG are compared to baseline patterns for that specific specimen/wearer. In an embodiment, a set of specimen/wearer baselines during different contexts are recorded and a specific baseline is selected for comparison.

In an embodiment, the specimen/wearer is a human and the magnitude of change and/or the rate of change of each of the SSG and the EVG, over short time points, indicate information about the psychological, emotional and stress states of the specimen/wearer. In an embodiment, measures of SSG over time are used to calculate heart rate variability and/or heart coherence.

In an embodiment, the devices of this disclosure include or connect with a device for measuring movement, a movement sensor. The movement sensor provides information about the movement context of the specimen/wearer. In one embodiment, the movement sensor includes an accelerometer. Information from the movement sensor is able to distinguish when the specimen/wearer is still, walking, running, shaking and many other physical movements. In an embodiment, the movement sensor is used as an indicator to inform the noise filtering threshold levels and in an embodiment is tuned real-time. The devices of this disclosure are useful waking and during sleep.

In an embodiment, the devices of this disclosure integrate into a smart watch or fitness wearable such as a Pebble watch and/or band. The devices of this disclosure can be incorporated into and/or presented in wrist devices, wristwatches, wrist bands, the Pebble watch, patches, clothing, belts, buttons, underwear bands, jewelry, headwear, hair clips, earphones, arm bands, and rings. Other methods known in the art are useful as well. In an embodiment, a device is not worn but leaned on or into from time to time, such as by pressing between fingers or toes. In an embodiment, a device of this disclosure is in a toe or finger ring.

In an embodiment, devices of this disclosure are useful for mammals, including humans, dogs, cats, etc. In an embodiment, the devices of this disclosure are waterproof.

In an embodiment, devices of this disclosure have a mode that includes a visual graph-like indicator of pulse rate and/or heart rate variability. The specimen, a wearer, uses the device, similar to known biofeedback machines, letting them see visually the real-time feedback of whatever stress management technique they are using to calm themselves down.

The electrodes in devices of this disclosure are made from materials known in the art including carbon impregnated silicon rubber, plated metal, stainless steel, silver, gold, hydrogel, dry electrode, wet electrode, suction electrode or similarly conductive or capacitively coupled interface. In an embodiment, the signal from they specimen/wearer (21) is amplified and filtered by passive and active circuits (12-20). After signal conditioning is complete, the conditioned signals are optionally fed into a microcontroller (25) for processing, storage or analysis. In an embodiment, an analog reference (2) for the filters is generated by the first stage of the cascaded reference circuit. A reference signal which is (about half or) exactly half of the analog power supply voltage (5-6 and 9-10) is fed into an amplifier (8) but is not filtered and purposely contains power supply noise and other (typically) unwanted interference. The specimen/wearer reference is generated by the first (5, 6, 9, 10, 8) and second (3, 4, 7, 11) stages of the cascaded reference circuit and injected into the specimen (1). The noisy signal (5, 6, 9, 10) being fed (2) into the filters and amplifiers (12-20) is combined with an arbitrary signal (11) which may be supplied by the microcontroller (25) or equivalent and driven into the reference electrode (1) connected to the specimen/wearer.

Signals generated by the microcontroller (25) are superimposed and modified by the biological and physiological activity of the specimen/wearer (for example, 30). Analysis of the waveforms present after conditioning (24) and optionally analysis by the microcontroller (25) yields information about the specimen's biological and physiological condition.

The design of the devices and systems of this disclosure use active (24) and passive (27) techniques to eliminate noise by incorporating it into the reference system (27). Due to the design of the floating system, noise is significantly reduced relative to the sampling device (25). The disclosed approach is simpler, lower power and less noisy than traditional differential sensing techniques.

Device Learning Methods

In an embodiment, in order to derive or infer the specimen/wearer's physiological state from their biological signals, a learning system is used and included in the devices, systems and methods of this disclosure. In one embodiment, various biological signals are gathered from an acquisition device and parameterized. For example, when heart rate is measured, it is parameterized in beats per second. The parameterized data is streamed into a system that represents the data in a matrix. The matrix is correlated with previously obtained or measured matrices that are either predefined, captured automatically by the system, and or flagged by the specimen/wearer.

In one embodiment, the match percentage to previous matrix data is calculated by generating a simple correlation coefficient such as the Pierson correlation coefficient:

$$r_{xy} = \frac{\sum_{i=1}^{n}(x_i - \bar{x})(y_i - \bar{y})}{(n-1)s_x s_y} = \frac{\sum_{i=1}^{n}(x_i - \bar{x})(y_i - \bar{y})}{\sqrt{\sum_{i=1}^{n}(x_i - \bar{x})^2 \sum_{i=1}^{n}(y_i - \bar{y})^2}},$$

In another embodiment, it is calculated by advanced methods such as multidimensional cross correlation FFTs:

$F_R(f) = FFT[X(t)]$ $S(f) = F_R(f) F_R^*(f)$ $R(\tau) = IFFT[S(f)]$

The learning systems of this disclosure are useful for establishing normal baseline parameters by detecting the most common physiological signal input patterns. In an embodiment, once they are established, changes in the patterns are used to trigger an alert. A variety of external stimuli can cause changes to baseline parameters and in an embodiment, the devices are customized to include such changes to the baseline parameters and provide useful information as to the effectiveness of medication, therapy, marketing, processing of stressful events, change in health, disease state, effectiveness of exercise, response to food, allergies, people, activities, animals, etc. This disclosure provides methods for detecting and alerting the specimen or other entities of meaningful changes due to such experiences.

In an embodiment, recorded matrix segments are marked and categorized based on the feedback of the operator. For example, certain matrix segments are marked as "stressful experience," "anger," "calm," "allergic reaction" or any other physiological experience or name so the right baseline is used at the right time. In an embodiment, the wearer selects the baseline. In another embodiment, the device suggests which baseline to use.

Analysis and categorization of physiological states is an important step forward in helping people become more aware and more sensitive to their body and mind.

Devices, methods and systems of this disclosure provide real-time feedback that can be used to assist everyone in enhancing their own awareness of their physiological states and related emotional states. People can learn their own early warning symptoms indicating rising stress levels. People can learn to identity their own personal internal and external triggers of distress, stress as well as eustress or potentially "good" stress. Feedback can be used to facilitate learning of the use of techniques (breathing, meditation, thought-stopping, shifting their attention, etc.) to calm themselves.

In an embodiment, the specimen chooses to and/or the device is programmed to aim for a selected range, quantity and/or quality of stress that optimizes eustress or good stress while minimizing bad stress or distress.

In an embodiment, the devices and systems of this disclosure are useful during the four basic steps for accomplishing behavioral change: real-time awareness of a problem, new behavioral tools for addressing the problem, feedback for fine-tuning one's use of the tools, and feedback during ongoing use over time so new behaviors become new habits.

In an embodiment, the devices, methods and systems of this disclosure are combined to create a mood interpretive system. This disclosure provides key components of a mood interpretive system. While this disclosure specifically measures EVG and SSG, the devices can also be adapted to measure other characteristics known in the art but not limited to HRV, skin moisture, skin impedance, galvanic skin response, ECG, EKG and/or movement.

In FIG. 1, a power supply (5, 6, 9, 10) is used to generate a noisy reference. A simple reference is generated by dividing the positive power supply rails (9, 10) using a resistor divider (5, 6). In one embodiment, resistors 5 and 6 may be replaced with resistive elements such as MOSFETs or other circuit element with resistive properties. A low pass filter is optionally created by adding a capacitor parallel to resistor (6), as is known in the art. The filter corner frequency of the network is set to less than about half of the open loop bandwidth of the amplifier (8). In one embodiment the bandwidth of the capacitor in is set to less than $\frac{1}{5}$, $\frac{1}{10}$, $\frac{1}{100}$ or $\frac{1}{1000}$ of the amplifier (8). The amplifier (8) is configured in the unity gain configuration.

The output of the amplifier (8) outputs the strong noisy reference input to the amplifier (7). The base noisy reference is typically used internally, but in certain applications may be fed out to the specimen as well.

An arbitrary waveform is injected (11) and mixed with the base noisy reference with resistors (3, 4). Ratiometrically, typically resistor (4) will be small compared to resistor (3). The weak or small, mixed signal is fed into the amplifier (7) in the unity gain configuration with the same configuration as the amplifier (8). The strong or large reference signal comes out of electrode (1) to be fed into the specimen. In some applications, the output of the electrode (1) is used internally by the device in amplification and/or filtering elements (24).

The cascaded references of this disclosure are useful in many devices and systems known in the art and as yet to be invented.

In an embodiment of this disclosure, the specimen/wearer provides self-reported mood data that may be used for calibrating, comparing, analyzing, creating a baseline or other techniques known in the art. In embodiments, the specimen/wearer is exposed to various stressors to test the device, create baselines, calibrating, etc. In an embodiment, this disclosure provides a mood index and/or a stress index whereby the mood and/or stress level of the specimen/wearer can be determined or suggested. In an embodiment, physiological and self-reported mood data along with other activity and demographic and psychographic data is collected from many users/patients to create new indexes.

In an embodiment, the devices, methods and systems of this disclosure communicate with and/or utilize data from an accelerometer. In an embodiment, devices and systems of this disclosure includes an accelerometer.

In an embodiment, the devices of this disclosure have a noisy reference. In an embodiment, this noisy reference is cascaded. In an embodiment, this reference is a patient reference signal. In an embodiment, the devices of this disclosure are configured to fit on a wrist, forearm, finger, hand, ankle, foot, toe, calf, or other appendage. In an embodiment, the devices, methods and systems of this disclosure are designed to make physical and/or electrical contact with the wearer's skin. In an embodiment, the devices of this disclosure are used on non-human animals. In an embodiment, the devices of this disclosure are designed and configured to sufficiently accurately measure EVG and SSG despite the possible presence of muscle artifacts and/or motion artifacts.

In an embodiment, the devices of this disclosure do not utilize plethysmography. The devices of this disclosure are configured to detect changes in skin surface charge and/or spectral current transmission. In an embodiment, the spectral analysis includes analysis of more than one waveform, more than two waveforms, more than five waveforms, and more than 10 waveforms. In an embodiment the devices and systems of this disclosure detect energy changes in the cells of or near walls of blood vessels. In an embodiment, the devices of this disclosure measure electrical changes when blood passes through a vessel or when a blood vessel stretches as blood passes through it. In an embodiment, the devices of this disclosure are able to measure stretch of cells in or near a muscle. The devices of this disclosure are able to accomplish short vector activity measurements continuously, approximately continuously or at time points and they provide short vector recordings and data storage of cardiac activity, and/or infinitesimally small vector activity measurements and recordings or data storage.

In an embodiment, there are many different types and magnitudes of signals a specimen/wearer can choose from. In an embodiment, the specimen/wearer can select from a predetermined range or a specimen/wearer can determine the levels of various measurements that trigger a signal to be sent to themselves and/or other people, equipment, etc.

This disclosure provides algorithms for determining likely moods, magnitudes of moods, etc. In an embodiment, the algorithms are customized and useful for one person, and in another embodiment, the algorithms are useful for many people.

This disclosure provides methods for measuring physiological traits of a specimen/wearer and taking one or more actions resulting in increasing the likelihood that a business transaction will take place. In embodiments, the action comprises delivering advertising to the specimen/wearer, delivering the user's info to a business owner, delivering sample products to the specimen/wearer, and/or alerting a health care practitioner such as a coach about possibly checking in on the specimen/wearer.

The devices of this disclosure provide means for communicating with, sending information to, and collecting information from other devices, methods and systems. In an embodiment, the information is about breath or a breathing characteristic, movement or activity and other physiological characteristics known to be measured and/or reported on in the art.

In an embodiment for children, a watch having a device of this disclosure shows a smiley face when the child is calming and a scared (or other) face when the child is getting more stressed.

When a "device(s) . . . of this disclosure" is stated, it optionally includes devices, methods, compositions and/or systems of this disclosure.

1 Embodiment Example

In an embodiment of this disclosure, a device creates a voltage action potential that is sensed between two electrodes. The input electrode is connected to a filtering network with the other side connected to the cascaded reference system. The filtering network is comprised of the following:

A high pass filter that removes the DC offset of the electrodes and low frequency muscle artifact noise. The high pass filter works by blocking unwanted low frequencies. The high pass filter also provides a means of protection by blocking DC leakage currents.

A low pass filter that diverts radio frequency interference into the cascaded reference system—cancelling it out.

An additional low pass filter diverts unwanted high frequency noise and muscle artifact into the cascaded reference system—cancelling it out.

The filtering network is attached to a single ended OpAmp (operational amplifier) in the unity gain configuration. The amplifier has a small resistance in the feedback path to increase phase margin and stability. The single ended OpAmp in the unity gain configuration is connected to high pass filter, further reducing unwanted offsets and low frequency muscle artifact noise. The filter shunts the unwanted signals to the cascaded reference system.

The high pass filter is connected to an inverting high gain amplifier in a Butterworth low pass filtering configuration. Unwanted high frequency artifact is removed from the signal during the filtration and amplification stage. The Butterworth configuration of the amplifier significantly increases stability during the high gain amplification process.

The high gain amplifier is connected to an anti-aliasing filter which feeds a computer controlled acquisition system. The anti-aliasing filter decreases high frequency noise by providing a stable signal input during computer controlled sampling events.

The computer controlled acquisition system performs digital filtering and processing of the input signal. Algorithms may analyze the acquired data and categorize the content. The content then may be transmitted to a companion device such as a watch.

The cascaded reference generator is composed of two OpAmps in the unity gain configuration. The first OpAmp generates a noisy reference signal derived from the power supply rails. Since the noise from the power supply is shared with the reference signal the configuration eliminates most power supply noise typically experienced by the signal input chain.

To enable the SSG measurement, an additional amplifier is cascaded in front of the first amplifier. The second amplifier generates an output signal comprised of the output of the first amplifier mixed with an arbitrary signal generated by a microcontroller or other processing element.

Passive filters are connected to the first amplifier, while active amplification and filtering elements are connected to the second stage of the cascaded reference generator. The different signal connections superimpose the arbitrary waveform on top of the noisy reference. If the input electrodes are shorted, the arbitrary waveform will not be detectable. During normal use, the user will attenuate the arbitrary waveform in a manner which reveals information about their physiological condition. Spectral analysis of the arbitrary waveform is conducted to determine specimen/wearer states and physiological condition. The arbitrary waveform can be adjusted in a real time by the processing element to provide more fine-grained information about the specimen's/wearer's physiological condition.

The cascaded reference is unique in that it can utilize an open loop system—feedback is not required to ensure the input signal stays within the limits of the system—as this is intrinsically accomplished by the architecture of the above amplifier, reference generation and filtering stages.

This disclosure provides circuits for providing a noisy cascaded reference, these circuits including, but not limited to (in this application, except for when something is explicitly limited, including means included, but not limited to): with a) a first reference generator including: a first pair of resistors configured to inject a driven first reference containing a DC voltage and power supply noise to a second reference generator and b) the second reference generator including: a second pair of resistors configured to inject a driven second reference containing the combined output of the first reference generator and an arbitrary input into a specimen. In an embodiment, the order of these reference generators is swapped, the DC voltage and power supply noise (or equivalents known in the art) has the driven second reference injected into it. In an embodiment, these references are cascaded in any order. Additional references may be added.

In an embodiment, there are no noise filtering components in the devices or systems of this disclosure. In an embodiment, there is a subset of the standard set or an incomplete set of noise filtering components in the devices and systems of this disclosure. In an embodiment, the circuit is configured to be electrically connected to an organism, and in an embodiment that organism is a human. In an embodiment the circuit further includes a protection resistor configured to be in series with the organism. In an embodiment the circuit further includes a capacitor in parallel with one of the resistors in the first pair of resistors, creating a low-pass filter.

In an embodiment, the circuit is configured to measure very fine, delicate, small, low amplitude and/or hard to see signals from the specimen. In an embodiment, the devices of this disclosure provide information that indirectly describes how well the specimen transmits energy at different frequencies.

An embodiment of the disclosure provides a low amplitude signal sensing circuit including a) a cascaded reference circuit including: i) a first reference generator including: a first pair of resistors configured to inject a driven first reference containing a DC voltage and power supply noise to a second reference generator and ii) the second reference generator including a second pair of resistors configured to inject a driven second reference containing the combined output of the first reference generator and an arbitrary input, together a cascaded reference, into a test object and b) a sensing circuit configured to be electrically connected to the cascaded reference circuit through the test object including: i) one or more sensing electrodes configured to receive electrical stimulus from the test object, the stimulus including a low amplitude signal and ii) a filter that is configured to reference the cascaded reference thereby making the low amplitude signal more detectable and measurable.

In an embodiment, circuits of this disclosure are configured to detect characteristics useful for determining a heart rate and related physiological characteristics of a test object or specimen. In an embodiment, the circuits of this disclosure have fewer then 4, 3, fewer than 3, 2-3, or only 2 electrodes that electrically connect to the specimen. In an embodiment, the first electrode delivers the reference signal (s) to the specimen, a reference electrode, and the second electrode receives signal(s) from the specimen, a sensing electrode.

An embodiment of the disclosure provides a circuit for sensing an electrovesselgram (EVG) signal including: a) a first circuit for providing a cascaded reference including: i) a first reference generator including: a first pair of resistors configured to inject a driven first reference containing a DC voltage and power supply noise to a second reference generator and ii) the second reference generator including: a second pair of resistors configured to inject a driven second reference containing the combined output of the first reference generator and an arbitrary input into an organism and b) a second circuit for acquiring EVG signals, electrically connected to the first circuit, including: i) one or more sensing electrodes configured to receive a signal from the organism, ii) a low-pass filter configured to receive the organism signal from the one or more sensors, iii) a first amplifier configured to receive the low-pass filter output, iv) a high-pass filter configured to receive the first amplifier output and v) a second amplifier configured to receive the high-pass filter output and configured to output an amplified and filtered EVG signal. In an embodiment, the circuit for sending EVG signals also includes a reference to the second amplifier from: the first reference generator, the second reference generator, and/or both the first and second reference generators.

In an embodiment, the second circuit in the circuit for sensing EVG is configured to be electrically connected to the first circuit through the organism. In an embodiment, the reference circuit and the sensing/receiving and conditioning circuit are, independently of the specimen, electrically connected to each other. In an embodiment, the second circuit, the sensing or receiving circuit, further includes a protection resistor configured to be in series with the one or more sensing electrodes. In an embodiment, the second circuit further includes an AC coupling capacitor configured to be in series with the one or more sensing electrodes. In an embodiment, the second circuit further includes a second low-pass filter after the second circuit.

In an embodiment, the first circuit is configured to provide the cascaded reference proximal to where the one or more sensing electrodes receive the organism signal. Proximal means, as it is used in the art, near. The referencing/delivering and receiving/sensing electrodes are configured to be proximal enough to each other and a blood vessel such that useful signals from the blood vessel area including potentially modified reference signals are available and received/sensed by the sensing/receiving electrode. Examples of configurations of proximal useful in the practice of this disclosure are shown in FIG. 5, however these are not necessarily drawn to scale. In particular, the electrodes are likely much smaller than shown.

In an embodiment the first circuit and its reference electrode and one or more sensing electrodes are configured to be proximal, close enough, to a blood vessel in the specimen.

In an embodiment, the conditioning circuit has the low pass filter, the first amplifier and/or the second amplifier referenced to one or more of the first reference generator, the second reference generator, or both the first and second reference generators. In an embodiment, the second amplifier includes a second low-pass filter.

An embodiment of the disclosure provides a method for creating a cascaded reference including: a) providing DC voltage containing power supply noise, b) providing a first reference generator including a first pair of resistors and an amplifier, c) scaling the DC voltage containing power supply noise through the first pair of resistors and the amplifier to produce a noisy reference, d) providing an arbitrary waveform, e) providing a second reference generator including a second pair of resistors configured to receive the arbitrary waveform and the noisy reference, and f) combining the noisy reference with the arbitrary waveform in the second reference generator to produce a cascaded reference. In another embodiment, the arbitrary waveform reference is cascaded into the noisy waveform reference. In an embodiment, the cascaded reference is configured for injection into an organism.

An embodiment of the disclosure provides a method for sensing an electrovesselgram (EVG) signal including: a) providing a cascaded reference including i) providing DC voltage containing power supply noise, ii) providing a first reference generator including a first pair of resistors and an amplifier, iii) scaling the DC voltage containing power supply noise through the first pair of resistors and the amplifier to produce a noisy reference, iv) providing an arbitrary waveform, v) providing a second reference generator including a second pair of resistors configured to receive the arbitrary waveform and the noisy reference, and vi) combining the noisy reference with the arbitrary waveform in the second reference generator to produce a cascaded reference configured for injection into an organism; b) providing an EVG signal receiving circuit including: i) providing one or more sensing electrodes configured to receive a signal from the organism, ii) providing a low-pass filter configured to receive the organism signal from the one or more sensors, iii) providing a first amplifier configured to receive the low-pass filter output, iv) providing a high-pass filter configured to receive the first amplifier output; and v) providing a second amplifier configured to receive the high-pass filter output and configured to output an amplified and filtered signal including EVG; c) electrically connecting the EVG signal receiving circuit to the organism; d) electrically connecting the cascaded reference to the organism; e) injecting the cascaded reference into the organism; f) electrically connecting, independently of the organism, the EVG signal receiving circuit to one of the group consisting of the first reference generator, the second reference generator and both the first reference generator and the second reference generator; and g) in a continuous time system filtering, amplifying and referencing the organism signal including: i) receiving the organism signal with the one or more sensors, ii) delivering the organism signal to the low-pass filter and low-pass filtering it, iii) delivering the low-pass filtered signal to the first amplifier and first amplifying it, iv) delivering the low-pass filtered, first amplified signal to the high-pass filter and high-pass filtering it, v) delivering the low-pass filtered, first amplified, high-pass filtered signal to the second amplifier and second amplifying it to produce an amplified and conditioned signal, and vi) referencing the amplified and conditioned signal to the cascaded reference; and h) providing an amplified and conditioned EVG signal.

In an embodiment, the method for sensing an EVG signal includes electrically connecting and injecting the cascaded reference and electrically connecting the EVG signal receiving circuit proximal to a blood vessel in the organism.

In an embodiment, the method for sensing an EVG signal includes connecting and injecting the cascaded reference on approximately one side of the local longitudinal axis of the blood vessel and connecting the EVG signal receiving circuit to the organism on approximately the other side of the axis.

In embodiments, the delivering/referencing and sensing/receiving electrodes are either 1) approximately adjacent to the blood vessel approximately in line with each other on either side of the vessel, 2) diagonally opposed from each other, on either side of the blood vessel, 3) in line with and over the blood vessel, and 4) in line with each other and offset longitudinally (or laterally) from the blood vessel. Alternatively, the electrodes are longitudinally offset and laterally offset on one side of the blood vessel.

In an embodiment, the method includes comparing two or more EVG signals measured at two or more time points to determine the differential voltage generated by expansion and contraction of one or more cells of the blood vessel. In an embodiment, the differential voltage is the difference between the maxima and minima of the measured EVG signals.

In an embodiment, the method also includes measuring the one or more cells in the wall of the blood vessel. In an embodiment, the method also includes contacting the organism on a limb or appendage. In an embodiment, the method also includes contacting a wrist.

In an embodiment, the method also includes measuring a frequency spectrum of the amplified and conditioned EVG signal.

An embodiment of the disclosure provides a method for sensing a subdermal spectrogram (SSG) signal including: a) sensing an EVG signal, b) extracting a sensed arbitrary waveform, and c) performing a spectral analysis of the sensed arbitrary waveform. Performing a spectral analysis of the sensed arbitrary waveform is done by techniques known in the art including but not limited to DFT and FFT.

In an embodiment, extracting a sensed arbitrary waveform is done by subtracting the injected arbitrary waveform. The method for sensing an SSG optionally includes applying filtering about simultaneously with extracting the sensed arbitrary signal.

An arbitrary waveform is input and spectrogram is performed on the sensed signal to detect more physiological characteristics and states. In an embodiment, the presence of chemical markers is predicted. In an embodiment the method includes extracting and comparing signals with a microcontroller. In an embodiment, the organism signal is sensed, simultaneously filtered and amplified, about simultaneously the injected arbitrary waveform is subtracted, and the results are presented in a spectrogram. Specifically more than one signal to make a spectrum of signals that is measured and presented. In an embodiment, the method for measuring SSG includes performing a spectral analysis of the sensed signal.

In an embodiment, the cascaded reference has more than 2, more than 10, more than 100 or more than 1000 waveforms, approximately simultaneously, and the waveforms differ in one or more characteristics including phases, wavelengths, voltages, and amplitudes. In an embodiment, the arbitrary wave does not include a continuous sine wave. In an embodiment the arbitrary wave is not derived from DC. In an embodiment the methods of this disclosure do include performing impedance measurements as the amount of skin conductance, drop in voltage or change in the electrical resistance of the skin are not measured.

An embodiment of the disclosure provides a method for detecting the EVG of a person including the person putting a watch containing a device of this disclosure on their wrist, the person living their life, the watch repeatedly injecting a cascaded reference, sensing s signal from the person that includes the EVG signal, conditioning the EVG containing signal, and delivering that signal to a microcontroller and optionally other components for storage and/or analysis. The disclosure also provides a method for detecting the EVG and SSG of a person as described above that also includes injecting a cascaded reference that includes an arbitrary waveform, sensing the person's signal that includes EVG and SSG, extracting the sensed arbitrary waveform (that is likely modified in transmission), and performing a spectral analysis of the sensed arbitrary waveform.

This disclosure provides methods for determining a mood or a change in mood of a person including measuring EVG and SSG of the person either at various time points and/or comparing a set of EVG and SSG results to a baseline of similar results correlated with moods, and correlating these to predict the mood or change in mood of the person. In an embodiment, the mood is the amount and/or type of stress. This disclosure provides methods for measuring the quality and quantity of stress experienced by a specimen.

In an embodiment the person's EVG and SSG are measured about continuously. In an embodiment, the EVG and SSG are measured, the data is separated into two or more time points, and the data from two or more time points is analyzed to determine the person's mood at the first time point relative to the second time point. In an embodiment, the method includes receiving, filtering and amplifying a first amplified and conditioned signal at a first time point; receiving, filtering and amplifying a second amplified and conditioned signal at a second time point, referencing the second EVG receiving circuit amplified and filtered signal to the cascaded reference, and calculating, comparing and/or deriving to determine a characteristic of the EVG that changes between time points.

In an embodiment, the devices, systems and methods of this disclosure utilize, connect with devices that measure and/or include measurements of movement, temperature, other vital signs, and/or breathing depth and/or rate with the aim of increasing accuracy of EVG, SSG and/or mood information.

In an embodiment, the methods of this disclosure include detecting movement and/or ignoring, tossing out or masking EVG, SSG and/or mood data if ambient movement is too great. Similarly, the methods may include detecting changes in temperature and/or ignoring, tossing out or masking EVG, SSG and/or mood data if temperature quantity or rate of change is too large. Alternatively quantities and/or rate changes in temperature are used to confirm or refute mood determinations.

This disclosure provides methods for detecting a physiological characteristic including the steps of delivering a cascaded reference to a specimen, receiving a signal from the specimen, conditioning (e.g., filtering, amplifying) the signal, measuring the signal and correlating data about that signal with stored data about physiological characteristics.

An embodiment of the disclosure provides methods for detecting a physiological characteristic selected from the group consisting of: EVG, SSG, EEG, moods and stress. In an embodiment, the methods of this disclosure include selecting a physiological trait to measure and selecting a filter setting of a device of this disclosure to measure that physiological trait. In an embodiment, selecting a filter setting includes setting the filter maximum to about 100 KHz, about 10 KHz, about 10 KHz, about 1000 Hz, about 250 Hz, about 100 Hz, less than 100 Hz, less than 90 Hz, less than 80 Hz, less than 50 Hz, less than 30 Hz, and/or less than 20 Hz and/or setting the filter to a range selected form the group consisting of about a 100 Hz range, a 75 Hz range, a 50 Hz range, a 30 Hz range, a 20 Hz range and a 10 Hz range. In an embodiment, the frequencies measured are between 10-500 Hz, 50-100 Hz, 30-80 Hz, 10-60 Hz, 5-40 Hz, or 4-20 Hz. In an embodiment the filter is set to allow measuring if frequencies between 100-250 Hz, between 250-1000 Hz, between 1-10 KHz, or between 10-100 KHz. Different filter setting may be selected for measuring physiological characteristics of the brain, heart, and/or muscle.

This disclosure provides methods for detecting blood vessel differential voltage. In an embodiment, methods for detecting blood vessel differential voltage includes detecting the difference between charges at two electrodes contacting a specimen by comparing them directly to each other. In the devices of this disclosure used for detecting differential voltage, there is a small isotropic self capacitance and very small parasitic capacitance due to small device size. Differential voltage is determined by measuring differences at the two electrodes relative to one another and/or measuring patterns of change of both over time.

In the methods, systems and devices of this disclosure, electrodes are configured to be far enough apart from each other that a relevant difference is measured and close enough that there is not too much noise or artifact in the measurements.

In various embodiments of this disclosure, the devices, circuits and systems are configured to fit in a wrist strap, to fit in a watch band, to work as part of smart watch, to be body worn, and to be isolated from earth or a common ground. In an embodiment, the methods include isolating the circuits, devices and systems from substantial, interfering earth ground.

In an embodiment, the devices, systems and methods of this disclosure are able to wirelessly communicate with other devices.

This disclosure provides a device with at least 2 electrodes located proximal to a blood vessel, the first to inject a cascaded reference, the second arranged to sense and measure the differential voltage compared to the first electrode about continuously over time points without using a common or earth ground, wherein the differential voltage is primarily generated by the expansion and contraction of cells in the wall of one or more blood vessels in the specimen electrically connected by the by the electrodes. In an embodiment, the differential voltage is primarily generated by other cells and/or physiological processes, and the differential voltage measured correlates with heart rhythms of the specimen.

This disclosure provides devices for measuring one or more physiological characteristics selected from the group consisting of EVG, SSG, galvanic skin response and skin impedance, wherein the device including fewer than 4 electrodes, fewer than 3 electrodes, only 2 electrodes, at least 2 electrodes, and 2 or more electrodes.

This disclosure provides a system for measuring physiological states of an organism, such as quantities and qualities of stress, that include: a) an EVG and SSG monitoring device, b) a microcontroller with stored code for recording, storing transmitting data, and optionally c) a stored database on signals and stress, d) a microcontroller that includes an algorithm for performing analysis of signals detected by the device and comparing that analysis to the database and determining the physiological state of an organism.

In an embodiment, the systems of this disclosure include devices of this disclosure. In an embodiment, the systems of this disclosure include a microcontroller configured to send out data and/or information on physiological states of an organism to an accessory such as a watch, a flash card, a blue tooth transmitter, etc. In an embodiment, the physiological state is stress.

In an embodiment the devices, systems and methods of this disclosure are configured for measuring physiological states of an organism, for measuring the mood of an organism, measuring the change in a mood of the organism, for measuring the quantity or quality of a mood, for measuring stress, and/or for creating correlations between measurements and moods. In an embodiment the devices, systems and methods are for determining primary mood states or ordering a range of secondary mood states. In an embodiment, the mood or mood state is selected from the group consisting of stressed, distressed, eustressed, angry, aggressive, calm, and/or combinations thereof.

In an embodiment, the devices, systems and methods measure, calculate and/or use information about a parameter of a specimen selected from the group consisting of: environmental data, movement, activity level, self-reported mood, self-reported amount of stress, self-reported type(s) of stress, breathing quantity, breathing quality, breathing rate, breathing depth, body temperature, skin temperature, heart rate, heart rate variability, amount of activity, type of activity, blood oxygen levels, blood pressure, pulse oximetry, pupil size/change, voice characteristics/changes, muscle tension, chemical markers (e.g., in sweat, in blood, saliva), skin moisture, skin conductance, skin impedance, and galvanic skin response.

This disclosure provides devices, systems and methods for measuring the frequency spectrum of an EVG.

In an embodiment, signals, data or measurements determined by the devices, systems and methods of this disclosure are compared to signals, data or measurements selected from the group consisting of:
  from the same specimen/wearer from a previous time point,
  calculated or averaged from many measurements of the same specimen/wearer,
  calculated or averaged from one or more other patients/users,
  from the same specimen/wearer doing the same activity,
  from the same specimen/wearer doing a different activity, and
  from the same specimen/wearer on a different part of the body at about the same time.

In an embodiment, a first set of two or more signals, data or measurements of SSG and EVG determined by the devices, systems and methods of this disclosure about a wearer are compared to a second set of signals, data or measurements of SSG and EVG determined by the devices, systems and methods of this disclosure and a step is performed selected from the group consisting of: providing data on the comparison to the user, secondly comparing the comparison to a threshold and alerting the wearer about the second comparison to the threshold. In an embodiment, the devices and systems of this disclosure are configured to and the methods include steps for informing and or alerting a wearer about their measured and/or analyzed signals, data, mood, etc.

In an embodiment the devices and systems of this disclosure are configured to and method includes steps for placing these devices and systems on an organism far enough away from the organism's heart to eliminate substantial interfering muscle noise including cardiac muscle noise, respiration noise, motion artifact, and/or electrode sensing noise. In an embodiment, the devices, systems and methods are used on an organism's limb or appendage. In an embodiment, the appendage is selected from the group consisting of: wrist, forearm, finger, thumb, upper arm, ear, calf, ankle, knee, foot, toe, neck, and tail. In an embodiment, the devices and systems of this disclosure are configured to be in a necklace, earring, ring or other form of jewelry.

This disclosure provides a method for producing a subdermal spectrogram (SSG) signal waveform comprising: a) providing a cascaded reference comprising i) providing DC voltage containing noise selected from the group consisting of: power supply noise, system noise, and both power supply noise and system noise; ii) providing a first reference generator comprising a first pair of resistors and an amplifier; iii) scaling said DC voltage containing power supply noise through said first pair of resistors and said amplifier to produce a noisy reference; iv) providing an arbitrary waveform; v) providing a second reference generator comprising a second pair of resistors configured to receive said arbitrary waveform and said noisy reference; and vi) combining said noisy reference with said arbitrary waveform in said second reference generator to produce a cascaded reference configured for injection into an organism; b) providing an SSG signal receiving circuit comprising: i) providing one or more sensing electrodes configured to receive a signal from said organism; ii) providing an amplifier configured to receive said signal and configured to output an amplified signal; c) electrically connecting said SSG signal receiving circuit to said organism; d) electrically connecting said cascaded reference to said organism; e) injecting said cascaded reference into said organism; f) electrically connecting, independently of said organism, said SSG signal receiving circuit to one of the group consisting of said first reference generator, said second reference generator and both said first reference generator and said second reference generator; and g) simultaneously amplifying and referencing said organism signal comprising: i) receiving said organism signal comprising a version of said arbitrary reference with said one or more sensors; ii) delivering said signal to said amplifier and amplifying it; iii) extracting the received arbitrary waveform from said organism signal or said amplified signal; iv) referencing said amplified signal to said cascaded reference; and v) performing a spectral analysis of said sensed arbitrary waveform; and thereby providing an amplified SSG signal waveform.

In an embodiment the specimen is a test object.

An embodiment of the disclosure includes a wearable including a first reference generator, a second reference generator, a first electrode, and a second electrode. In one embodiment, the first reference generator is coupled to a power supply (e.g., 10) and the first reference generator is configured to output a first reference signal (e.g., output of 8 or node between 5 and 6) that includes power supply noise generated by the power supply. In one embodiment, the power supply is a DC power supply.

In an embodiment, the second reference generator includes an amplifier (e.g., 7) having a first input node and an output. The second reference generator is coupled to receive the first reference signal from the first reference generator at the first input node of the amplifier. The amplifier is also coupled to receive an arbitrary input at the first input node of the amplifier.

In an embodiment, the first electrode (e.g., 1) is configured to contact a skin surface of a specimen (e.g., 30) and the first electrode is coupled to receive an output signal from the output of the amplifier (e.g., 7)

In an embodiment, the second electrode (e.g., 2) is configured to contact the skin surface of the specimen and the second electrode is coupled to receive the first reference signal.

In an embodiment, a second input of the amplifier (e.g., 8) is coupled to receive the output signal from the amplifier, as illustrated in FIG. 1.

In one embodiment, the first reference generator includes an optional amplifier 8 configured to amplify the first reference signal, as illustrated in FIG. 1. The first reference signal may be received from the output of amplifier 8. The second electrode may be coupled to receive the amplified first reference signal from the output of amplifier 8.

In an embodiment, a cascaded reference including an arbitrary waveform is injected into a tissue sample. The sensed signal includes the arbitrary waveform as modified by the tissue sample, and the sensed signal is measured and visualized by spectrogram, which provides information about the tissue. The devices and methods of this disclosure are useful for assessing many different types of specimen, not only mammals, organisms, components derived from mammals and organisms, etc. They are useful for assessing human-created materials as well.

This disclosure also provides methods for making, testing, determining baselines, and using the devices and systems of this disclosure. In an embodiment, devices and methods of this invention are used to increase, optimize and/or hold about steady a quantity and/or quality of eustress, or good stress.

All methods and visualization of data, real-time presentation of data, and alerting specimens/wearers that are known in the art can be practiced with the devices, methods and systems of this disclosure. Data on a specimen/wearer can be gathered throughout a time period, such as a day, and presented in real time or afterwards in line graph to show changes in stress and/or in the characteristics measured or calculated from them during the time period.

Psychotherapy and Coaching

Devices, methods and systems of this disclosure are helpful in psychotherapy, life coaching, and health and wellness coaching with individuals, couples and families. This disclosure is used both in sessions and between sessions for training clients to identify internal and external triggers and to learn how to calm their autonomic nervous systems. In sessions, therapists/coaches use them to assist individuals in identifying and tracking which thoughts and behaviors are creating stressful reactions and then use this information and biological feedback to learn to decrease stress. With couples, this disclosure assists in providing real time feedback to interrupt internal distress that leads to conflict. Couples learn to interrupt the fight or flight response and are able to more easily resolve conflicts and facilitate productive conversations. Parents use this disclosure to assist in staying out of reactive mode (another way of describing the fight-or-flight response, and are instead response-able) so they parent more from conscious choice than from reaction. This disclosure assists PTSD sufferers in recognizing early signs of flashbacks and regressive episodes, similarly to how PTSD assist dogs support people—by recognizing symptoms so early. This disclosure helps in identifying triggers, interrupting them at an early phase before an anxiety attack can build and assists in people learning how to get into a calm state of being. Research indicates that stress plays a role in the worsening of virtually all mental health symptoms. Real-time feedback using the devices, methods and systems of this disclosure play an essential role in maintaining mental health stability in people with mental health diagnosis.

Coaching—Identifying the Most Stressful Topic

A client comes in to a life coach's office. The client complains of vague symptoms of depression, anxiety, poor sleep, over busy work, and some conflict at home. The therapist offers the client a device of this disclosure to wear during the session. The client puts on the device. As the client shares with the therapist about his/her week at work and home, the device is monitoring his/her biometrics. As the client talks about his/her stressful work concerns, the device does not indicate that s/he is in substantially increased distress/stress over what is typical of a client coming in to the life coach's office. As s/he begins to describe a situation at home, the device indicates that his/her stress level is increasing. This assists the client and coach in focusing the session on the situation at home that was creating the most distress/stress for the client.

Health Care

Individuals with chronic diseases such as cancer, heart disease, diabetes, autoimmune disease use the devices, methods and systems of this disclosure to maintain a calm state that facilitates their healing. They heal faster, more thoroughly and more deeply and experience better outcomes, fewer side effects and fewer recurrences. Some patients decrease use of medication. Patients feel more personal presence and power over their own health care options, choices and results. By decreasing the amount of stress they experience, patients spend less on health care, their insurance companies spend less on their health care, and society in general spends less on health care.

Cancer Patient—Making Decisions

An oncologist offers the use of a device of this disclosure to his/her patients during consultations. His/her patient, a woman diagnosed with breast cancer, wears a device of this disclosure during her appointment. Whenever the device alerts, the patient and the physician pause their conversation and focus on diaphragmatic breathing techniques to bring her adrenaline and stress levels down. This facilitates her more fully understanding her options and making better medical decisions that are more aligned with her values (rather than making reactionary decisions from her fears).

Predicting Panic Attacks During Sleep

A patient wears a device of this disclosure while sleeping. The device picks up changes correlating with an oncoming panic attack. The device directly, or indirectly by transmitting to another device such as an alarm clock or computer, creates a noise or vibration or some other signal that slightly (or substantially) awakens the sleeper and prevents the panic attack or night tremor.

PTSD #1

A soldier returns from combat. S/he is diagnosed with PTSD. S/he is receiving counseling and is on antidepressant medication. S/he wears a device of this disclosure nearly all the time. It often alerts him/her to his/her rising stress level that s/he is unaware of. Because the device is monitoring him/her and then bringing what is happening in his/her unconscious state to his/her conscious awareness, s/he is now able to engage in normal daily activities like grocery shopping, discussing household issues with his/her partner, helping his/her kids with homework, and looking for work. Since the device serves as an early warning signal, s/he is able to pause and utilize stress management techniques that allow him/her to calm down and function—and lead the life s/he chooses, despite having PTSD.

PTSD #2

A former soldier with PTSD wears a device of this disclosure every time s/he leaves his/her house. S/he goes to the park with his/her dog. Two young children begin fighting in the playground. The device lets the former soldier that his/her stress level is increasing. The former soldier, aware that s/he is growing distressed, chooses between going back home and doing some stress management techniques to calm him/herself down. S/he feels more comfortable leaving the house now because s/he can catch his/her stress/distress before s/he is completely overwhelmed and terrified.

Recovering Addict

A recovering addict wears a device of this disclosure. In the past s/he would feel stressed and be tempted to take a drink. Sometimes in these situations, s/he would have a drink of alcohol. Wearing a device, s/he notices when s/he feels stressed and takes other actions to reduce his/her stress. His/her stress levels never get as high as when s/he does not wear this device. As a result, s/he less frequently drinks alcohol and maintains his/her sobriety for longer stretches of time.

Detecting Allergies & Toxins

People with allergies and chemical sensitivities, some environmental and some due to ingestion of certain foods, are exposed to various potential allergens and environmental toxins while wearing devices of this disclosure. The devices alert people quickly, almost immediately, when they are having a psychosomatic response to a test. The devices alert them after about 2-15 minutes of exposure when they are actually physically allergic to the item tested. By correlating specific physical symptoms, amount stress and timing of stress, psychosomatic vs. actual allergies are distinguished. Also, people are able to gauge how severe their allergies are. They are able to notice more subtle allergies and sensitivities that they have not yet noticed from other specific physical symptoms (e.g., digestive upset) by wearing devices of this disclosure.

Diabetes

A person is give a device of this disclosure and takes note of stress levels simultaneously while measuring blood sugar levels on a blood sugar monitor. The patient is then able to compare and notice the impact of stress on blood sugar. The patient is then more motivated to keep stress levels low as part of treating their diabetes.

Couples Therapy & Relationship Dynamics

A couple comes into a therapist's office. The therapist offers both the partners devices of this disclosure to wear. As one tells the therapist what issue s/he wants to discuss, the other partner's device indicates his/her stress level is increasing. The therapist uses that as a cuc to assist the listening partner in using some breathing techniques to calm him/herself. After a few minutes, the device indicates that the listener is calmer. The therapist asks the speaker to continue to discuss his/her concern. After a few moments, the listener's device indicates his/her stress is growing again. The therapist works with the listener to calm him/herself again. This time the therapist suggests the listener continue to deeply breathe while his/her partner talks. This time the listener is able to stay calm and hear his/her partner's concern. (In the past, s/he would have begun yelling at him/her before s/he finished expressing his/her concern.) Throughout the session, the therapist uses the cues from the device to know when to interrupt the couple and have them focus on calming themselves down before continuing the conversation, thus allowing the couple to have a productive conversation about a high-conflict topic. The couple is given the option to purchase devices to wear at home to continue to practice calming themselves down when needed.

Circling

Groups of people gather to do a social meditation called Circling (as practiced by a group called Authentic Portland, using a derivative form of Circling by Guy Sengstock). Previously, one participant got reactive, triggered and very stressed when another participant's share reminder him/her of bad experiences in childhood. The triggered participant got very loud, angry and aggressive which brought up fear and stress in the other participants too. The next week when they circle again, all the participants wear devices of this disclosure. This time, when challenging topics are brought up that remind the previously aggressive participant of childhood, he/she gets alerted by the device and remembers to breathe more deeply, to move their spine, to remember and make subtle movements in their body confirming that this is here and now, not back then (techniques from Gay & Katie Hendricks, www.Hendricks.com), and he/she was able to relax and not get aggressive. He/she was then able to respond (not react) to the speaker's share. When this happens, sometimes other participants' devices alert them to their own increase in stress when they see the previously aggressive and now presencing themselves group member, take steps to calm him/herself down. Over time, everyone in the group becomes more able to stay present, everyone scares themselves less and less with connections to memories, and everyone's stress baselines go down. The group becomes that much more creative and joyful.

Mental Health—Schizophrenia, Bipolar, Autism Spectrum, Executive Functioning Disorders A patient with schizophrenia (as do some patients with severe bipolar disorder and autism spectrum disorders) typically gets easily overwhelmed by strangers. S/he purchases a device of this disclosure and is trained on how to use it to indicate the early stages of stress/distress. S/he goes to the grocery store and a stranger begins talking to him/her. His/her device vibrates letting him/her know s/he is growing stressed/distressed even though s/he is not consciously aware that s/he is growing stressed. S/he decides to leave the store and come back later, thus keeping his/her psychosis from getting out of control.

Mental Health—Panic Attacks

A person suffering for years with intermittent panic attacks begins using a device of this disclosure. The device lets him/her know when s/he is beginning to feel anxiety. S/he then uses his/her meditation, visualization, and breathing techniques s/he has learned from his/her yoga teacher, therapist, and meditation teacher. After 3 months of using the devices, now even without using the device, s/he is beginning to recognize his/her internal physical indicators of the beginning of anxiety.

Parenting

A parent comes in to a therapist's office crying, as s/he has been yelling at his/her kids and does not want to. The therapist sells/rents him/her a device of this disclosure to wear at home. The parent wears the device at home while cooking dinner. As s/he is cooking, his/her children begin to bicker. Within moments, the device is vibrating to let the parent know his/her stress level is rising. The parent chooses to do a visualization that the therapist taught him/her. The device indicates his/her stress level calming. The parent then redirects the children, having one help him/her in the kitchen and the other get started on his/her homework. In the past, s/he would have gone into a fight-or-flight state and yelled at the children. S/he would have felt helpless and bad about him/herself, leading to lowered esteem and depressed mood. Now that s/he has the device to assist him/her in catching his/her early signs of stress, s/he is able access more choice in how to respond rather than just react.

Fertility Treatments

A couple having trouble getting pregnant comes in to see their doctor. The doctor realizes that their problems likely stem from the woman trying to get pregnant being too stressed. The doctor gives her a device of this disclosure to wear during her waking hours. This women becomes aware of how stressed she is feeling throughout her day and evening. She cuts back on and stops some activities that create much of her stress. She eats a healthier diet and eliminates risky chemicals that contribute to her stress, including chemicals mimicking hormones. She also learns stress management and reduction techniques and begins to implement them. Her stress levels decrease substantially. Within 2 months of decreased stress, she becomes pregnant. It is later proven that reducing stress—be it chemically or emotionally caused—substantially increases fertility in women.

Higher Apgar Scores and Baby/Mother Outcomes

Pregnant mothers wear devices of this disclosure. Those who use the devices to monitor and take actions to reduce the stress they experience while pregnant give birth to babies with higher Apgar scores right after birth. These mothers also have easier, less problematic labors and deliveries, reducing the number of C-sections. The babies and mothers are both healthier than controls. Over the next 10 years, these babies grow up to have lower rates of autism, autism-spectrum disorder, bipolar disorders, and a range of other challenges including AMID, as compared to controls.

Prison—Inmates, Guards, Prison Routines and Decreases Recidivism

Inmates in a prison are all given a device of this disclosure to wear throughout the day. The device indicates to the prisoner when s/he is beginning to become stressed. Prisoners choose to respond to the device's alert and calm themselves down. Information from the devices is uploaded into a computer program analyzing patterns for individual prisoners and for patterns in the prison community as a whole. The data analyzer is able to assess which prisoners are having success utilizing the biometric information to calm themselves down and taking them out of the fight-or-flight response.

These prisoners are offered more classes on meditation, biofeedback, yoga and other stress management tools to become even more successful at managing their stress. The prison warden is given overall statistics on patterns of arousal and stress. These patterns are mapped onto the daily schedule. The warden is able to determine which daily activities are increasing stress in the prison. The warden and staff are able to change the structure of activities in order to facilitate more calm in the prison in general.

Recently released prisoners who have used the device in prison are given a device of this disclosure to wear when released. This leads to a decrease in aggressive thoughts, aggressive behavior, recidivism and increased ability to function in their communities.

Prison guards are given devices of the disclosure to wear to work. They use the biometric feedback to know when to employ stress management techniques. The data is sent to a computer to be analyzed to assess overall patterns related to which job tasks are most stressful and induce the highest increases in adrenaline for the guards. Adjustments in the routines and structures of the prison are made accordingly to decrease stress in the prison for guards and prisoners.

Stress Predictions

A specimen/wearer connects their device of this disclosure (wirelessly, through an isolated interface, through the internet or directly to their computer) to their calendar. The device (or software that integrates with the device) compares their recent stress patterns with previous events on their calendar. Predictions are now made for their upcoming day and week about which times of the day and/or which days are likely to be more stressful. This allows the specimen/wearer to take actions to prevent and decrease their likely upcoming stress, such as removing events, rescheduling activities, adding time for calming activities, etc.

Driving

People wear devices of this disclosure while driving and subsequently stay calmer and more alert. If they become stressed, they are notified of such by vibrations, but interruptions in their music and other methods known in the art. Accidents decrease. Truck drivers use the devices to inform themselves if they are sufficiently decreasing in stress and alertness that they may be getting too sleepy to drive.

Sports

Athletes use the devices of this disclosure to achieve the optimal level of stress and improve their game. Athletes are able to easily achieve the sweet spot of alertness without troublesome anxiety.

Games—Practice Calming in Stressful Situations

Adolescents are given a device of this disclosure to wear. They watch a brief video, read written instructions, or receive a brief lesson utilizing a mode of the device that functions as real-time biofeedback. They practice the biofeedback to learn how to calm themselves down. They then utilize the device to monitor their stress level while playing video games. When the device biometrics indicate a certain level of stress, the adolescents pause the game to practice the biofeedback and reduce their stress. Over time they work up to being able to utilize the biofeedback mode of the device while they are playing video games, thus maintaining drastically lower stress levels than their peers playing the same games. Their game performance improves.

Adults also use games as a way to practice noticing and decreasing their stress in the moment while participating in an activity.

Games—Improving Performance

Garners wear a device of this disclosure to maintain their sweet spot (an ideal state of alertness below a distress threshold) in order to play their best games. In an embodiment of this disclosure, each gamer sets the device to a specific eustress stress level and/or bad stress level of their choice. In an embodiment, methods and devices of this disclosure include ways to record and track game performance with stress level to help the player determine their optimum sweet spot or eustress level.

Games—Practicing for Real Life

The adolescents are then given video games that mimic real life situations such as peer pressure, divorcing parents, having limited financial resources, violence, choices about illegal drugs, learning to drive, parental conflict, and while wearing a device of this disclosure, they learn how to negotiate difficult real life situations while remaining calm.

The adolescents then wear a device of this disclosure throughout their day, not just while playing games, and apply what they have learned to real life situations so they are less stressed, cause less drama, etc.

First Responders #1

Police, firefighters military and other emergency personnel use devices of this disclosure to assist in reestablishing equilibrium after a crisis has been resolved. After a situation has occurred, they put on a device of this disclosure and set an after crisis baseline stress level. They then monitor how successful they are at reducing their stress level and returning to a normal baseline. When they are not successful, they are alerted to and do use alternative tools to calm themselves. The methods and devices of this disclosure optionally include an algorithm for an ideal rate of stress decrease and means for alerting the user if this rate is not achieved and/or surpassed. This has positive impacts on the overall physical and mental/emotional health of the first responders: it decreases their need and tendency to self-medicate with alcohol, improves relationships with family members, and decreases divorce rates. This decreases the impact that unaddressed stress has on first responders' personal relationships, personal health care, work relationships and job performance.

First Responders #2

A policeman has had a particularly scary day at work intervening in a domestic violence situation that involved a gun. It resolved peacefully and no one was hurt. After completing all the required paperwork, the policeman leaves the station. As soon as s/he is in his/her car, s/he puts on a device of this disclosure, which indicates to him that his/her body is indeed as adrenalized as s/he feels. S/he takes five minutes in the car and calms himself with some creative visualization techniques s/he has learned. Feeling calmer (also verified by the device), s/he drives home. As s/he is driving, s/he begins to replay the scene in his/her head and imagining it having turned out differently. His/her mind begins to play out scary scenarios of a shooting conflict. His/her images are gory. The device alerts him/her that his/her stress level is increasing. S/he utilizes thought-stopping techniques and refocuses his/her attention on feeling his/her body as s/he drives. When it is safe, s/he pulls over and texts his/her partner. S/he lets him/her know that the day was harder than usual and that s/he is feeling stressed. S/he does this so s/he will not be blindsided when his/her partner gets home. S/he does a few more minutes of calm breathing before resuming his/her drive home. The device indicates his/her stress level is calming down and that his/her adrenaline levels are decreasing. S/he goes home and is greeted by his/her intentionally calm and caring partner. The combination of stress management training and the device alerting him/her to his/her physical-emotional state prevents him/her from taking his/her stress out on his/her wife and/or drinking too much alcohol—his/her previous and ineffective strategies for dealing with work stress.

Education—Special Ed

Each student in a special education class is given a device of this disclosure to wear during school. There is a quiet low-stimulation corner in the classroom where the students are allowed to go to calm themselves down. A student is working independently while the teacher and aid are helping other kids. The student does not know how to do a math problem. S/he asks the teacher for help. The device lets the student know s/he is beginning to get stressed, in his/her case frustrated, while waiting. The student chooses to go to the quiet corner and listen with headphones to calming music while waiting his/her turn for the teacher's attention. In the past, this student would have had a tantrum disturbing everyone in the class. In this case, the teacher comes to get him when it is his/her turn, and s/he is calm and ready to receive help.

Students and Teachers

Students use the devices, methods and systems of this disclosure to self monitor behavior, thereby catching early signs before acting out and being disruptive. Students are able to self-monitor academic anxiety. Teachers assess their own stress levels and calm themselves down leading to an improved academic and social environment for themselves and students. There is decreased burnout. Children learn their own early warning signs and prevent stress, anxiety, resulting disruptive behavior, distractions and worse academic performance.

Education—First Grade

A class of first graders are all given devices of this disclosure to wear during school hours. By the end of the year, 80% of the students can recognize their inner signals and sensations of early stress/distress and have learned effective techniques to calm themselves.

Education—Teaching

A teacher wears a device of this disclosure while teaching. Whenever the device indicates that s/he is growing stressed, s/he and his/her class take 3 deep breaths. His/her class has fewer behavior problems than any class s/he has ever had. S/he feels less stress at the end of the day and greater job satisfaction. Because his/her energy isn't being used to manage behavior issues, s/he has the energy to be more playful and creative in how s/he teaches his/her students.

Education—Type A Students

Type A personality students are trained in self-calming techniques. They are then given devices of this disclosure to wear during important exams such as SAT tests and final exams. They score higher on tests and have less post-exam illnesses than their Type A control peers who do not use these devices and have higher adrenaline levels.

Meditation #1

A meditator wears a device of this disclosure and it indicates how calm the meditator becomes, thus s/he is able to assess how effective his/her meditation techniques are and make changes accordingly.

Meditator #2

A meditator learns various meditation techniques while wearing and using a device of this disclosure. The meditator assesses which new techniques work well for him and his/her style and which don't.

Meditator #3

A meditator begins the day with meditation and establishes a baseline. S/he then set a wearable device of this disclosure to indicate whenever his/her biometrics indicate a stress level 20% higher than during his/her deep meditative state. Throughout the day the device then lets him/her know whenever s/he has risen to that level of stress. S/he then utilizes meditation techniques for a brief period of time until his/her stress level decreases. Over time his/her baseline stress level decreases and s/he is able to decrease the frequency of experiences that s/he goes over his/her 20% threshold.

Business People

Someone pitching a new business to a potential investor is alerted by their device, which privately lets them know that they're getting a little anxious. They use the tools suggested to successfully calm themselves down leading to a higher chance of success making the sale. The devices of this disclosure are used to decrease high stress levels with thereby increases productivity in the office. Creativity is increased as well.

Professional Setting—Sales Meeting

A person who works at an advertising business wears a device of this disclosure as s/he pitches ideas to his/her new clients. S/he uses the feedback from the device in order to calm herself down which in turn helps him/her to be more articulate. S/he lands the client. In business, particularly in sales, it is ideal to aim for some eustress while minimizing bad stress.

Business Team Dynamics—A Meeting

In a business team meeting, each team member is wearing a device of this disclosure on their wrist or ankle. As they listen and speak, they are able to track their stress levels. As one of them has their stress increase, they receive a subtle vibrating signal near the device and also receive a message on their communication device (e.g., devices of this disclosure can include or communicate with wireless devices). This allows this team member to realize they are feeling increased stress and choose to take actions to calm themselves. This allows them to more fully and more consciously participate in the meeting. This also supports them to acknowledge they don't like something being said and that they want to speak up and share a differing opinion. In an embodiment, the devices, systems and methods of this disclosure distinguish between stress arising from fear and stress arising from disagreement with and dislike of something and they provide different types of signals. When both types of responses/reactions are occurring, this is deciphered and is communicated to the specimen/wearer as well. Meetings are more productive because participants feel less stress and are more present, and also because participants realize sooner when they have something to say and speak up. This prevents and minimizes drama and distraction. It keeps everyone on focus, on point, and in easy communication and interaction with each other. In another embodiment, the devices of this disclosure notice and alert unexpected decreases in healthy stress or eustress during a meeting and alert the specimen/wearer that they may be daydreaming about something pleasant instead of paying attention to the meeting and topics being discussed.

Meeting Breaks

A business team or community group meets and everyone in the meeting wears devices of this disclosure. Their data is wirelessly sent to a centralized computer and analyzed. A non-stress inducing alert goes off letting everyone know when a maximal threshold of stress is reached in the room, typically a sufficiently higher level of stress by at least a specified percentage of people, letting everyone know it is time to take a break.

Health & Auto Insurance Costs

Businesses and or health insurance companies provide discounts on health insurance when people wear devices of this disclosure and practice calming tools. Auto insurance rates go down when drivers wear or install devices of this disclosure in their cars and practice calming when their stress increases when behind the wheel.

The following documents are incorporated into this specification by reference:

U.S. Pat. No. 8,666,672 B2 Determining a user's psychological state using body temp, skin temp, heart rate, blood oxygen levels, and skin moisture U.S. Pat. No. 8,617,067 B2 Using an environmental sensor and one or more of a mood sensor, a heart-rate monitor, a blood-pressure monitor, a pulse oximeter, or an accelerometer to monitor stress levels U.S. Pat. No. 8,622,900 B2

U.S. Pat. No. 8,216,136 Monitors BP and HR and alerts care provider of patient's condition U.S. Pat. No. 8,285,356 Adherent, one or more electrodes checking impedance, ECG and acceleration U.S. Pat. No. 8,301,232 Electrodes in a smart phone case checking ECG signals for cases of arrhythmia etc.

U.S. Pat. No. 8,374,688 Adherent device checking tissue hydration/tissue resistance/impedance, at least 4 electrodes, for long term patient monitoring U.S. Pat. No. 8,412,317 Device measuring impedance of tissue, at least 4 electrodes for patient monitoring U.S. Pat. No. 8,500,635 System for monitoring mental health conditions, using voice patterns, BP, stress level and HR, providing an interactive instructional routine U.S. Pat. No. 8,679,008 Handheld, checking electrodermal activity to determine the user's stress level for purposes of stress management U.S. Pat. No. 8,285,370 B2 Microcontrolled ECG monitor using an electron pair and injecting circuit noise U.S. Pat. No. 8,239,012B2 Microcontrolled ECG monitor using differential voltage and an electron pair, injecting circuit noise US 20120089000 A1 ECG monitor using a plurality of electrodes, for an adult female, attached to chest US20080214944 Apparatus receiving data relating to heart, measuring the effectiveness of mobile intervention in reducing anger or stress U.S. Pat. No. 8,961,415 Method, using data from a wearable sensor measuring body temp, HR and sweat rate and monitoring physical activity to make an assessment of the physiological condition of subject US20150126824 Apparatus attached to body of subject, with physiological sensor, monitoring hydration status U.S. Pat. No. 8,529,457 System of stress and relaxation management with one cardiac activity sensor measuring HRV, respiration sensor integrated into textiles and using a galvanic skin response sensor US20110183305 Behavior modification system using 1+ sensors to measure physiological or psychological or behavioral parameter WO2000028892A1 Wrist mountable monitor, using impedance electrodes measuring heart rate, respiration or body motion US20100217099A1 Method of monitoring HR, activity level, tympanic membrane temp and breathing rate to assess stress level; Headset device US20080208015A1 Apparatus monitoring of at least one of galvanic skin response, blond pressure, blood sugar, spirometry, respiration rate, speech characteristics, typing speed and errors, hormonal levels, caloric expenditure, and muscle tension and provides a mobile intervention, including breathing exercises Accordingly, it is to be understood that the embodiments of the disclosure herein described are merely illustrative of the application of the principles of the disclosure. Reference herein to details of the illustrated embodiments is not intended to limit the scope of the claims, which themselves recite those features regarded as essential to the disclosure.

The invention claimed is:

1. A circuit for sensing an electrovesselgram (EVG) signal comprising:
 a. a first circuit for providing a cascaded reference comprising:
  i. a first reference generator comprising: a first pair of resistors configured to inject a driven first reference containing a DC voltage and noise selected from the group comprising: power supply noise, system noise, and both power supply noise and system noise, to a second reference generator;
ii. said second reference generator comprising: a second pair of resistors configured to inject a driven second reference containing the combined output of the first reference generator and an arbitrary input into an organism;
b. a second circuit for acquiring EVG signals, electrically connected to said first circuit, comprising:
i. one or more sensing electrodes configured to receive a signal from said organism;
ii. a low-pass filter configured to receive said organism signal from said one or more sensing electrodes;
iii. a first amplifier configured to receive the low-pass filter output;
iv. a high-pass filter configured to receive said the first amplifier output; and
v. a second amplifier configured to receive the high-pass filter output and configured to output an amplified and filtered EVG signal;
wherein said first circuit is, independently of said organism, electrically connected to said second circuit.

2. The circuit of claim 1, wherein said low pass filter and said second amplifier is referenced to said first reference generator output or said second reference generator output or said second reference generator output.

3. The circuit of claim 1 wherein said second circuit is also configured to be electrically connected to said first circuit through said organism at two points that are:
on an appendage selected from the group comprising of: wrist, forearm, finger, thumb, upper arm, ear, calf, ankle, knee, foot, toe, neck, and tail.

4. The circuit of claim 1 wherein said first circuit is configured to provide said cascaded reference within 5 inches to where said one or more sensing electrodes receive said organism signal.

5. The circuit of claim 1 that is configured to be body worn and configured to be isolated from earth ground.

6. The circuit of claim 1 further comprising one or more of the group comprising: a second circuit protection resistor configured to be in series with said one or more sensing electrodes, a second circuit AC coupling capacitor configured to be in series with said one or more sensing electrodes, and a second low-pass filter connected to the output of said second circuit.

7. The circuit of claim 1 that is configured to be contained on a flexible band.

8. The system of claim 7 that is configured to be worn on an appendage selected from the group comprising of: wrist, forearm, finger, thumb, upper arm, ear, calf, ankle, knee, foot, toe, neck, and tail.

9. The system of claim 7 that is configured with two sensing electrodes.

* * * * *